United States Patent
Broytman et al.

(10) Patent No.: US 9,574,180 B2
(45) Date of Patent: Feb. 21, 2017

(54) CELL THERAPY: A METHOD AND A COMPOSITION FOR TREATING DIABETES

(75) Inventors: Vladislav Broytman, Philadelphia, PA (US); Nikanor Broytman, Huntingdon Valley, PA (US); Nikolay Skaletskiy, Moscow (RU)

(73) Assignee: PHILADELPHIA MEDICAL SCIENTIFIC CENTER, L.L.C., Huntingdon Valley, PA (US)

( * ) Notice: Subject to any disclaimer, the term of this patent is extended or adjusted under 35 U.S.C. 154(b) by 1846 days.

(21) Appl. No.: 12/094,721

(22) PCT Filed: Apr. 17, 2007

(86) PCT No.: PCT/US2007/066786
§ 371 (c)(1),
(2), (4) Date: May 22, 2008

(87) PCT Pub. No.: WO2007/121438
PCT Pub. Date: Oct. 25, 2007

(65) Prior Publication Data
US 2008/0267925 A1    Oct. 30, 2008

Related U.S. Application Data

(60) Provisional application No. 60/792,929, filed on Apr. 17, 2006.

(51) Int. Cl.
A61K 35/39    (2015.01)
A61P 5/50    (2006.01)
C12N 5/071    (2010.01)

(52) U.S. Cl.
CPC ............ *C12N 5/0676* (2013.01); *A61K 35/39* (2013.01); *C12N 2500/02* (2013.01); *C12N 2500/90* (2013.01); *C12N 2509/10* (2013.01); *C12N 2523/00* (2013.01)

(58) Field of Classification Search
CPC ............................. C12N 5/0676; A61K 35/39
See application file for complete search history.

(56) References Cited

U.S. PATENT DOCUMENTS

| | | | |
|---|---|---|---|
| 5,741,334 A | * | 4/1998 | Mullon et al. ............. 623/23.64 |
| 2002/0071824 A1 | * | 6/2002 | Giannoukakis et al. .... 424/85.1 |
| 2004/0063200 A1 | * | 4/2004 | Chaikof et al. ............. 435/317.1 |
| 2005/0287129 A1 | * | 12/2005 | Cicciarelli et al. ......... 424/93.21 |

OTHER PUBLICATIONS

Kulkarni RH. 2004. The islet beta-cell. Int J Biochem Cell Biol 36: 365-71.*
Russell TR et al. 1984. Purification of beta cells from rat islets by monoclonal antibody-fluorescence flow cytometry. Cytometry 5: 539-542.*
Kharroubi I et al. 2003. Expression of adiponectin receptors in pancreatic beta cells. Biochem Biophys Res Comm 312: 1118-1122.*
Pipeleers DG et al. 1991. Transplantation of Purified Islet Cells in Diabetic Rats: II. Immunogenicity of Allografted Islet β-Cells. Diabetes 40: 920-930. Abstract only.*
Heath WR et al. 2001. Cross-presentation, dendritic cells, tolerance and immunity. Annu Rev Immunol 19: 47-64.*
"Immunogenic." MedlinePlus Merriam-Webster online medical dictionary. Available at <http://www.merriam-webster.com/medlineplus/immunogenic>. Accessed Mar. 9, 2015.*
Lafferty KL et al. 1983. Immunobiology of tissue transplantation: a return to the passenger leukocyte concept. Annual Reviews in Immunology 1: 143-173.*
Hirshberg et al., "State of the Art: Islet Transplantation for the Cure of Type I Diabetes Mellitus", Reviews in Endocrine & Metabolic Disorders, 2003; 4:381-389.
Inverardi et al., "Islet transplantation: immunological perspectives", Current Opinion in Immunology 2003, 15:507-511.
Osama et al, "Improved In Vivo Pancreatic Islet Function After Prolonged In Vitro Islet Culture", Transplantat, vol. 72 (11), pp. 1730-1736, Dec. 15, 2001.

* cited by examiner

*Primary Examiner* — Emily Cordas
(74) *Attorney, Agent, or Firm* — Caesar Rivise, PC

(57) ABSTRACT

A method of obtaining beta-islet cells from pancreases of rabbits and a composition for transplantation (xenografts or xenotransplants) of beta-islet cells isolated and cultured from rabbit pancreases to promote natural insulin production among people with diabetes.

6 Claims, No Drawings

CELL THERAPY: A METHOD AND A COMPOSITION FOR TREATING DIABETES

BACKGROUND OF THE INVENTION

1. Field of Invention

This invention relates to a cell therapy method and a composition for transplantation of beta-islet cells isolated and cultured from animal pancreases to promote natural insulin production among people with diabetes.

2. Description of Related Art

Type 1 diabetes affects more than one million Americans. Type 1 diabetes is the most severe form of the disease, in which the body's immune system attacks insulin-producing cells required to keep blood sugar at normal levels. It is known that extremely low blood sugar can result in seizures, impaired cognition, or unconsciousness. In the most severe cases, the complications are not well controlled by insulin.

Ideally, replacing insulin-producing cells in the pancreas can free diabetics from lifelong insulin injections and effectively cure the disease. The transplantation of these "islet" cells can now be done in two ways, through a whole pancreas transplant or through a less invasive and less costly process of injecting just the islet cells. Successful pancreas transplantation has been demonstrated to be effective in significantly improving the quality of life of people with diabetes, primarily by eliminating the need for exogenous insulin and frequent daily blood glucose measurements (Pancreas Transplantation for Patients with Type 1 Diabetes. Diabetes Care. 25 (Supplement 1): S111. January 2002). However, pancreas transplants require lifelong immunosuppression therapy to prevent rejection of the graft and potential recurrence of the autoimmune process that may destroy pancreatic islet cells.

The transplantation of beta-islet cells from donor pancreases has been shown to promote natural insulin production among patients with type 1 and type 2 diabetes (see Sperling, M. A. Type 1 Diabetes: Etiology and Treatment. Totowa, N.J.: Humana Press Inc. 2003. p. 529-552; Insulin Therapy. In: Edelman, S. V. and Henry, R. R. Diagnosis and Management of Type 2 Diabetes. Caddo, Okla.: Professional Communications, Inc. 2002. p. 121-148). Islet cell transplantation can be performed as a percutaneous minimally invasive procedure, in which islet cells are infused into the liver via the portal vein. However, like other transplant patients, islet recipients must take immune-suppressing drugs to prevent rejection of the foreign cells.

Xenografts or xenotransplants of islet cells derived from pork or beef has been studied and shown as required immunosuppression.

Ability of pre-cultured beta-cells of pancreases of newly-born rabbits to survive and to actively function in organism of xenogeneic recipient was demonstrated by us in experiments on rats with experimentally induced Diabetes Mellitus. (Skaletsky N. N. and others. 1994 {4}). Expressed and long-term (8 weeks—experiment term) anti-diabetic effect of xnotransplantation of cultures of islet cells as in cases of administering into abdominal cavity and spleen, and also in cases of administering it into transverse abdominal muscle. After experiments, histological tests were conducted that at the place of introduction of xenotransplants discovered islet cells with preserved structure and without signs of cellular immune reaction. At the same time, clear signs of regeneration of own beta-cells in pancreases of animals-recipients were detected. Beside a well-defined sugar-reducing effect, a well-defined medical-prophylactics effect of xenotransplantation of islet cells cultures on distinctive late complication f diabetes—Nephropathy,—was noted during experiments (Skaletskaya G. N. and others (2005 {4}).

RU 2135193 to Skaletsky at al. discloses obtaining beta islet cells from new-born rabbit pancreas and to transplantation methods. Beta cells are obtained by migration from pancreatic fragments in a culturing method requiring addition of serum to a culture medium.

Thus, despite of current developments, islet cells from different sources which would not require immunosuppression are needed.

All references cited herein are incorporated herein by reference in their entireties.

BRIEF SUMMARY OF THE INVENTION

Accordingly, one aspect of the invention comprises a method of obtaining beta-islet cells from pancreases of rabbits, the method comprising: (a) harvesting said pancreases of newborn rabbits and placing pancreases in a salt solution comprising an antibiotic at a temperature of 4-10° C.; (b) obtaining minced pancreatic micro fragments from said pancreases; and (c) incubating said minced pancreatic micro fragments in a serum free medium at a first incubation temperature 36.6° C. to 37° C. for a first incubation period and periodically replacing the serum free medium and removing spontaneously destroyed unwanted cells comprising exocrine cells and blood cells and elements of connective tissue until at least 80% of remaining cells are beta-islet cells; (d) and incubating said minced pancreatic micro fragments in said serum free medium at a second incubation temperature 22° C. to 29° C. for a second incubation period until at least 78-90% of remaining cells are beta-islet cells, wherein said serum free medium is optionally periodically replaced, and thereby obtaining beta-islet cells.

Another aspect of the invention comprises a composition comprising beta-islet cells obtained from rabbit pancreases, wherein beta-islet cells are isolated following a selected temperature regimen of incubation of minced pancreatic micro fragments obtained from said rabbit pancreases and cultured in a serum free medium in accordance with the above described method of the invention and wherein isolated beta-islet cells are obtained in a cell count amount of 1,500,000±100,000 and have viability of at least 80% and a pharmaceutically acceptable carrier. The pharmaceutically acceptable carrier suitable in this invention can include any suitable substance such as liquids, gels and solids which can be combined with the composition and recognized for its safety in administering to a mammal.

In certain embodiments, the composition comprises at least 50% of beta-islet cells.

In certain embodiments, the composition comprises at least 78% of beta-islet cells.

Another aspect of the invention comprises a use of the composition as described above to promote natural insulin production, the method comprising: preparing the composition of claim 6 comprising the beta-islet cells isolated and cultured from rabbit pancreases; and administering the composition of claim 6 to a subject in need of insulin and therefore promoting natural insulin production.

DETAILED DESCRIPTION OF THE INVENTION

The culture method of the invention include the use of a selected temperature regimen of incubation for minced pancreatic micro fragments obtained from a rabbit and cultured in a serum free medium. Following the method of the invention, a pure preparation of viable and active beta islet cells is obtained, which may be successfully transplanted to diabetic patient without the use of any immune suppression.

The culture method of the invention provides favorable conditions for the pancreatic beta cells and creates unfavorable conditions for ballast and immunogenetic cells (so-called passenger cells) such as, for example, exocrine, endothelial, dendritic, and lymphocytes. The elimination of all these passenger cells provides significant reduction of the immunogenicity of the cultured islet cells. Contrarily to the common belief that long-term cultivation of cells required addition of a serum supplement to the culture fluid, the inventor discovered that the use of serum free media in the method of the invention favors the growth of desired beta islet cells and disfavors the growth of unwanted passengers cells and therefore provides viable and active beta islet cells in a commercially valuable amount, wherein such cell are substantially free of unwanted passengers cells Without being committed to a particular theory, inventors believe that shedding of surface antigens also takes place, since there has been a remarkable lack of immune reaction despite the absence of any type of immunosuppressive therapy neither before nor after clinical islet cell xenotransplantation. As highly refined culture of beta-cells prepared by the method of the invention does not contain cells relating to donor vessels, so there is no rejection of xeno-transplanted beta-cells.

A synergistic combination of cells, solutions and conditions has been discovered by the inventors. This is accomplished by changing the environment, e.g., placement of the culture in $O_2$ incubator vs. 5% $CO_2$ incubator, varying the temperature and time intervals in the incubator over a period of 10-14 days. No genetic manipulations were used.

The culture technique and techniques of intramuscular transplantation of islet cell culture will now be described in detail. Rabbits are harvested by submerging in 40-96% ethanol, preferably 70% ethanol until the death is registered, e.g., for up to 10 min, preferably 7-8 min. In sterile conditions, a pancreas is removed from the abdomen cavity of a newborn rabbit (the term "newborn" as used herein includes rabbits from the time of birth to 5 days old rabbits which were not exposed to breast milk, preferably newborn to 12 h old rabbits) and immediately placed in a Petri dish with cold (e.g., 4-6° C.) Hank's salt solution or physiological solution (NaCl) and antibiotics (e.g., penicillin 1000 units/ml and streptomycin 10000 mg/ml). With the help of ophthalmic tweezers, a capsule of pancreas is removed; vessels and excretory ducts are removed. Next, the pancreas is cut by an ophthalmic scissors into micro fragments in the size of about 2-3 mm and then transferred to a special watch glass. Continue processing 18-20 pancreases in the above described manner. Next, pancreatic micro fragments are cut with the ophthalmic (corneal) scissors into smaller pieces, i.e., minced pancreatic micro fragments. The obtained minced pancreatic micro fragments are washed out with cold Hank's solution and placed in a culture flask or a bottle (e.g., space of 75 $cm^2$, Corning-Costar) distributing them on a surface of the bottom of the flask. 5-7 minutes later, during which there is an attachment of micro fragments to plastic, a serum free growth medium 199 (Sigma Aldrich) without a serum supplement is poured into the flask (e.g., 10% of a flask volume). The flask is then placed into an incubator with submission 0-5% $CO_2$ and pancreatic tissue is incubated at 36-37.5° C. (the first incubation temperature), preferably 36.6-37° C. for 6-10 days, preferably 7-8 days (the first incubation period). Every 1-2 days, the flasks with cultivated cells were observed through the inverted microscope and spontaneously destroyed exocrine cells of pancreas, blood cells and elements of connective tissue were removed; the growth medium 199 was replaced with a fresh growth medium. As a result of the first incubation period, islet cell clusters formed at the bottom of the flask and at least 78% of them (according to specific coloring) were pancreatic beta cells.

For the final clearing of ballast cellular elements initiating the immune response (e.g., leucocytes-passengers), culture flasks are placed in an incubator at temperature ranging from 22° C. to 29° C. (the second incubation temperature) for 4-5 days (the second incubation period). It has been observed that at the second incubation temperature of 24° C., the best results are achieved and the beta cell contain the least amount of passenger cells. After that the culture consisting only of islet cells 78-90% beta cells can be transplanted to a diabetic patient. In addition to islet cells, singular fibroblasts are found in the culture but their share, usually not exceeds 1-5%. Cells of epithelial origin are usually remaining cells in culture and make 5-17%, which fact the immune-histo-chemical coloring (with monoclonal antibodies against protein CytoKeratin 18) confirms; but they are not beta-cells, as these cellular structures are not revealing presence of insulin.

One dose of islet cell culture preferably containing 1,400,000-1,600,000 cells in a sterile suspension in Hank's salt solution (10-15 ml volume, not cranial, all cells obtained) can be placed to a plastic tube marked in an appropriate way. Islet cell culture made in accordance with the method of the invention (also referred herein as Beta Cells of Philadelphia Medical Scientific Center or BCPMSC) has following cell composition:

| | | |
|---|---|---|
| General cell count: | | 1,500,000 ± 100,000 |
| Beta cells | | 82 ± 8% (at least 50%) |
| Other islet cells | +30 | 9 + 2% |
| Fibroblasts | +30 | 2 + 1% |
| Progenitor (stem) islet cells | +30 | 7 + 3% |
| Cultivation is performed in serum-free growth medium 199. | | |
| Period of storage of BCPMSC: | | at 4-10° C. for 72 hours |
| | | at 11-24° C. for 48 hours |
| | | at 30-37° C. for 12 hours. |

The dose of islet cell cultures was prepared from 80 1-2 day old newborn rabbit's pancreases.
Term of cultivation—14-21 days.
Cell viability—82% or more is preferred.
At control incubation of the cultured islet cells, the insulin basal production has made 8400±1200 µU/ml/h, stimulated—16500±2700 µU/ml/h
The culture method of the invention excluded contamination of the culture by microorganisms (e.g., bacteria, fungi, mycoplasma and viruses).

Each dose will be accompanied with a certificate describing preparation having all necessary information on BCPMSC. Criteria for the isolation or elimination of diseased animals; as stated, at the first sign of any disease an animal is quarantined and is never returned back to the colony from quarantine.

The obtained culture can be transplanted to a recipient, e.g., a Diabetes Mellitus (DM) patient. The transplant (xenograft) or an injection can be administered by various ways, for example, by injection into the liver (i.e. directly into the hepatic parenchyma or through the portal vein), into pulp of the spleen, into the splenic artery, in specially performed large omentum pocket with use of laparoscopy technique, and intramuscularly. The preferred method of introduction of culture is into the rectus abdominis muscle of the recipient.

Transplanation Technique

With the injection needle, preferably not less than 7 cm in length and not less than 1 mm in diameter, the islet cell suspension is collected in a syringe and injected into the musculus abdominis rectus after local anesthesia. Preferably, the site of an injection is to be closed by sterile bandage.

Proof of Reduced Immunogenicity of the Islet Cell Cultures

Evidence in vitro: various histological experiments including light and electronic microscopy; immunohistochemistry, shown above, demonstrated that in the pure culture there are no so-called leucocytes-passengers (lymphocytes, macrophages and etc.) capable of initiating immune reaction after the procedure (9-12 month). Evidence in vivo: xenotransplantation of the islet cell culture into rats with an experimental diabetes leads to remission of the diabetic status for at least 30 days.

For the purpose of studying of immunogenecity of cells containing in the culture obtained through the above-described method from the pancreas of newly-born rabbits, there were experiments conducted to determine fixation of immune-globulins of human blood serum on them. Cells, incubated with various human blood serums were stained by monoclonal antibodies against human immune-globulins and analyzed on the flow cytometer. It appeared that cells containing in the culture are capable of fixating on their surface immunoglobulins M, but there were no immunoglobulin G fixation discovered.

A proper preparation of the diabetes patent for islet cell culture transplantation is recommended. Before the transplant treatment, a diabetic patient has to achieve as good glycemic state as possible by intensive insulin therapy. Patients should have no vaccinations and no serum therapy for 4 weeks prior to cell transplantation. Clinical research should include consultations of ophthalmologists, nephrologists, neurologist, vascular surgeon, dermatologist, diabetologist, and consultations of other specialists regarding secondary diabetic complications.

A patient can be prepared for islet cell xenotransplanation in the following manner:
 1. Elimination of ketoacidosis, frequent hypoglycemia or hyper-osmolarity by hospitalization, so that the patient's clinical condition will be compensated as possible;
 2. Maximal compensation of diabetic status, stabilization of blood sugar within normal or near normal levels by adequate insulin therapy under tight self-control of glycemia;
 3. Avoidance of vaccinations or serum therapy for 4 weeks prior to cell transplantation.

The following parameters will be followed in patients before and after the islet cell xenotransplanation, with the frequency as follows:

General:
 1. Level of HBA-1c (clycosylated hemoglobin) every 3 months;
 2. Level of C-peptide (basal and stimulated) every 3 months;
 3. Detection of auto-antibodies; anti-GAD, anti-insulin, anti-ICA;
 4. Serum cholesterol and triglycerides every 3 months;
 5. Home blood glucose self-monitoring (with diary) several times a day;
 6. Correction of insulin requirements (with diary).

Special:
Diabetic Retinopathy:
 1. Standard retinal fundal field evaluation by sterofundoscopic photography and fluorescent technique every 3 months;
 2. Visual acuity every 3 months.

Diabetic Nephropathy:
 1. Proteinuria/24 hr once a month;
 2. Microalbuminuria every 3 months;
 3. Serum creatinine every 3 months;
 4. Creatinine clearance very 3 (60 months;
 5. Blood pressure once a week.

Diabetic Neuropathy:
 1. EMG every 3 months;
 2. Nerve Conduction studies of tibial nerve; sural nerve; median nerve—every 3 (6) months
 3. Pain analog scale once a month;
 4. Orthostatic changes—once a month;
 5. EKG-r-r variation every 3 months.

Diabetic Vasculopathy:
 1. Doppler ultrasound every 3 (6) months;
 2. Doppler probe;
 3. Doppler Blood pressure ankle/arm;
 4. Doppler segmental blood pressure;
 5. Plethsmograph waveform change.

As biochemical and morphological research has demonstrated, cultures of pancreatic insular cells produced by the stated methods possess high secretory activity and sharply reduced immunogenic (immunological potency). A certificate of quality is preferably attached to each portion of cells designed for cell-therapy.

Indications and Contraindications for Xenotransplantation of Islet Cultures

Exemplary indications: (a) labile course of insulin dependent Diabetes Mellitus (IDDM) with inclination towards hypoglycemic status and/or ketoacidosis, (b) inability of reaching satisfactory compensation of IDDM by usual methods; insulin-resistance, (c) secondary complications of diabetes mellitus in patients with IDDM and NIDDM (neuropathy, nephropathy, retinopathy, angiopathy of lower extremities, etc.), excluding terminal studies, and (d) IDDM (insulin dependent) and NIDDM (non-insulin-dependent) without detection of secondary complications—for the purpose of prophylaxis.

B. Contra-indications: Acute infections & inflammatory diseases, or exacerbation of chronic diseases; Oncological Diseases.

Supervison of Patients after the Transplantation of Islet Cell Culture

Within the first year after transplantation, the above-stated inspection after 3, 6, 9 and 12 months is recommended.

The majority of recipients in 1-3 months after xenotransplantation demonstrate the following changes:
 1. Current/prior to XT—labile 1 type diabetes is stabilized;
 2. The bent of patients to ketosis disappears;
 3. Parameters of carbohydrate exchange (it is reduced daily average glycemia—in 1-2 months, the decrease of glycosylated hemoglobin content—3 months) improve;
 4. Decreases (for 20-30%) of requirement for exogenous insulin;
 5. Parameters of lipid metabolism improve:
 6. At recipients with absence of residual secretion of insulin by own beta cells (it is C-peptide not determined) appears the production of patient's insulin (C-peptide).

7. At patients with sensory motor neuropathy, pain and paresthesia disappear; parameters of sensitivity and conductivity of fibres of peripheral nerve improve. At patients with autonomic neuropathy, who struggle with glycemic control, postural hypotension, gastroparesis, and enteropathy (diarrhea), parameters of pulse and blood pressure are normalized, the functions of stomach and gut normalized too.

8. At 1 type diabetes patients with a stage expressed diabetic nephropathy (classification on C. Morgensen) decreases and disappears proteinuria, high blood pressure is reduced and normalized. At patients with a $3^{rd}$ stage of diabetic nephropathy, microalbuminuria decreases or becomes normal (less than 30 mg/day).

9. At patients with nonproliferated and preproliferated states of diabetic retinopathy, the clinical picture of a eye bottom is stabilized, the significant part of recipients have its improvement: haemorrhages resolve, the hypostasis of a retina decrease.

Stabilization of a diabetes mellitus course and the lowering of the exogenous insulin requirement result form the adequate functioning of transplanted islet cells and a partial recovery or increased function of islet cells of recipient's pancreas.

It is believed that the curative effect of transplanted cell cultures on the late diabetic complications is apparently explained by the restoration or strengthening of secretion by both transplanted and a patient's own beta cells of C-peptide, which is produced together with insulin and has a marked angioprotective effect.

According to hypothesis the development of microangiopathy, which is the basis of all diabetic complications, is due to the lack of C-peptide and some other hormone-like substances produced by the beta cells, which are absent at overwhelming majority of 1-type diabetes patients.

C-Peptide injection in patients with complicated 1-type diabetes mellitus results in the regress of secondary diabetic complications, such as nephropathy, retinopathy and neuropathy.

Transplanted rabbit's beta cells produce normal C-peptide, which has a physiological influence on late diabetic complications.

Table 1 demonstrates improved glycemic control and drop in insulin requirement following ICCXT (well-documented 112 cases).

TABLE 1

| Index | Before XT | Mo 3After | 6 Mo After | 9 Mo After | 12 Mo After |
|---|---|---|---|---|---|
| Average Daily Glycemia, mg/dl | 198 + 41 | 158 + 52 | 129 + 23 | 133 + 30 | 142 + 34 |
| HbAlc, % | 10.1 + 2.1 | 9.1 + 1.2 | 7.7 + 1.9 | 6.9 + 1.1 | 7.5 + 1.9 |
| Insulin Dose, IU | 56 + 11 | 38 + 15 | 25 + 12 | 32 + 9 | 40 + 8 |

Table 2 demonstrates insulin requirement (IU/day) and microalbuminuria (mg/day) level after repeated ICC XT in patient Ts.S (33 years old, 18 years of 1-type DM duration)

TABLE 2

| XT | Index | Before XT | 3 Mo After | 6 Mo After | 9 Mo After | 12 Mo After |
|---|---|---|---|---|---|---|
| $1^{st}$ | Insulin dose | 64 | 33 | 38 | 40 | 48 |
| | Micro-albuminuria | 936 | 680 | 348 | 330 | 496 |
| $2^{nd}$ | Insulin dose | 52 | 38 | 24 | 26 | 38 |
| | Micro-albuminuria | 660 | 377 | 189 | 199 | 167 |
| $3^{rd}$ | Insulin dose | 42 | 38 | 25 | 32 | 40 |
| | Micro-albuminuria | 330 | 145 | 99 | 112 | 88 |
| 4th | Insulin dose | 40 | 34 | 20 | 16 | 16 |
| | Micro-albuminuria | 66 | 45 | 34 | 40 | 39 |

The main advantage of transplantation of islet cells in comparison to the usual therapy of Diabetes Mellitus of the 1-type, are as follows:

Due to regularly performed transplantation, all recipients show decrease in progression of diabetic angiopathy, and reversion of initial stages of late diabetic complications (retinopathy, nephropathy, neuropathy, and angiopathy), which is impossible to achieve with the help of usual therapy (injection of insulin upon self-control of glycemia, and traditional treatment of angiopathy).

This happens mostly because the transplanted beta-cells after the transplant taking (acceptance) start to produce in a recipient's body an angio-protective matter C-peptide, which a patient was deprived due to the collapse of his own beta-cells (due to auto-immune assault).

Ability of cultures of pancreatic insular cells, received through the original method from pancreas of newborn rabbits, to survive and function in in-vivo environment, ahs been demonstrated by us in experiments of xenotransplanatation of such cultures to animals with experimental Diabetes Mellitus.

Vistar Line male rats of body mass of 180-220 gm, regularly fed, were used as experimental animals.

Experimental Diabetes Mellitus was provoked by sub-dermal application of Alloxan (dosage 200 ml for 1 kg of body weight) or by sub-dermal application of Streptozotocini (dosage 60 ml/kg).

During experiments and control probes we used only rats with Alloxan or Streptozotocin-induced Diabetes, those whose level of hypoglycemia on empty stomach was 20 mmol/l and higher. Earlier conducted tests indicated that such animals did not have spontaneous reversion of experimental Diabetes Mellitus.

After transplantation of P.I.C. cultures, 88 out of 104 rats with stable or sever Alloxan-induced Diabetes Mellitus (almost 85%) displayed firm remission of diabetic status up-to the end of experimental term (20 weeks). Firm decrease of blood sugar levels of almost-up-to-normal levels was registered in blood of animals-recipients. At the same time, characteristics clinical symptoms of diabetes were also vanishing (such as weight loss, polydipsia, polyuria). Anti-Diabetic effect of xenotransplantation was clearly demonstrated both in cases of application of cultures into liver (through portal vein or directly into liver's parenchyma) and also into spleen (cultures were brought in intra-pulp), and also through the abdominal muscles. Even after 8 weeks after xenotransplantation, P.I.C. with preserved structure and with signs of secretory activity was detected in places of implantation in rats with remission of experimental Diabetes.

During special series of experiments the role of preliminary cultivation of P.I.C. into vitro was demonstrated clearly in survival of cells in organisms of xenogeny recipient. For that purpose, we performed comparative analysis of results of xenotransplantation of cultures of P.I.C. of pancreas of human fetuses and xeno-transplantation of non-cultivated fetal Island tissue to rats with experimental Diabetes Mellitus. It was detected that sugar-reducing effect is more expressed and long-lasting in cases of transplantation of pre-cultivated P.I.C. in comparison with transplantation of non-cultivated tissue of Pancreas, which results only in short-lived remission of Diabetic status. So, the immune-modulating result of cultivating in vitro was experimentally proven to significantly increase the term of survivability in an organism of alien recipient.

Pancreases of 18 rats-recipients, on whom successful xenotransplantation of cultures of Pancreas of newborn rabbits had been performed, were subjected to histological exam in 8 weeks after transplantation. For that purpose a fragment of pancreas was fixated in Buena solution and was drown in paraffin. Slices (5-7 mkm thick) were colored by hematoxilin and eosin, and also by Aldegid-Fuxin for revealing of β-cells. At the same time, pancreases of 6 control animals who had untreated alloxan-induced Diabetes as well as pancreases of 6 healthy rats (no Alloxan applied) were closely examined.

While examining pancreases of healthy intact rats, some 45-76% of β-cells, as expected, were found in "Langerhans" islands. Rats with untreated Alloxan-induced Diabetes had sharply decreased amount of β-cells in Islands—in average 8.3+−1.1%.

Significantly higher amount of β-cells in Islands was discovered in rats-recipients. In animals, who had been subjected to xenotransplantation of P.I.C. cultures, their own Pancreases displayed typical β-cells and its share among "island" cells was from 10 to 55% (some from 7 to 21%) (average 23.5+8.8).

With regards to these experiments, we may assume that anti-diabetic effect of xeno-transplantation of OK cultures on developments of experimental diabetes in rats is occurring 2 general ways: a) Functioning of transplanted β-cells, confirmed in addition to expressed sugar-reducing effect, also by revealing groups of transplanted P.I.C. in the pulp of spleen of animals-recipients: b) Stimulating effect of transplantation of P.I.C. cultures on the Island apparatuses of pancreas of rats-recipients, which possibility is confirmed by data histological exams revealing existence of significantly frequent of Islands with normal β-cells and bigger share of them in Islands of pancreas of rats-recipients than of rats with untreated Alloxan-induced Diabetes.

Successful experimental research became grounds for performing clinical transplantation of cultures of pancreas of newborn rabbits to Diabetes-type-1 patients.

Clinical Transplantation of Cultures of P.I.C. Produced Out of Pancreases of Newborn Rabbits.

Total of 112 patients with Type-1 Diabetes Mellitus (IDDUM) were under well-documented dynamic supervision.

Of total of 112 patients there were 58 men, and 54 women. Patients' age at the moment of transplantation varied from 16 to 53—average 35 years old.

It is known that severity of manifestation of secondary diabetic complications depends significantly on duration of the disease IDDM. Supposedly, destruction of own β-cells of the patient as a result of autoimmune process approximately happens on the $5^{th}$ year after manifestation of the disease. Secondary diabetic complications manifest itself usually in patients with duration of the disease of more than 10 years. Because of that, all IDDM patients were divided in 3 groups in reference to duration of the disease: a) 1 to 5 years—16 people; b) 6 to 10 years—43 people c) more than 10 years—53 patients. All patients had been examined with the aim to determine character of development of IDDM and establishing presence of diabetic complications.

Usually cultures received through the above-described methods out of 50-60 pancreases of 1-2 day newborn rabbits were used for transplantation for one patient. Suspension was usually delivered into transverse abdominal muscle under local anesthesia. No immune suppression was used.

The most important fact confirming an anti-diabetic effect in islet cells transplantation just because of functioning of transplanted beta-cells, is the fact of discovering them at the place of administering the transplantation. If after intra-peritoneal transplantation it is almost unreal to locate applied cells in the abdominal cavity, then after administering into the spleen it is possible, although very difficult.

A microphotograph of colored histological section through the spleen's pulp was obtained which clearly demonstrates a transplant represented by a group of epithelial cells in the center of the photo. Assurance that these cells are indeed a transplant is based, partially on the grounds that epithelial structures are absent in splenic tissue.

Accordingly, presence of epithelial cells in lineal pulp bears evidence to "incomer from outside", in this case—a transplant.

Based on the results of the scientific-experimental research, the several basic conclusions can be made:

1. Streptozotocin (Stz) makes general destructing effect on beta-cells of islets of pancreas, but at the same time, directly or indirectly leads to a loss of other islet cells.
2. It appears that a regeneration process in affected Langerhants islets happen mainly on account of recovery of beta-cells pool.
3. Islet cells cultures produced from pancreases of newborn rabbits through the original method consist generally of beta-cells cleared of ballast cellular elements and have a very high insulin-producing activity.
4. An intra-peritoneal, as well as intra-splenetic xenotransplantation of islet cells cultures to rats with experimental Streptozotocin induced Diabetes Mellitus, provides, in majority of cases, a stable remission of diabetic status for a duration of at least 8 week period.
5. Post-transplantation sugar-decreasing effect is secured as by functioning of transplanted beta-cells, also by insulin-producing activities in, to some degree, restored pool of beta-cells in islets of pancreases of rats-recipients. This is confirmed by findings of measuring concentrations of exogenous (rabbit's) and own (rat's) insulin in the blood of experimental animals.
6. Histological examinations of pancreases of experimental rats confirmed the expressed stimulation of regenerative processes in islets of rats with Streptozotocinal Diabetes Mellitus after administering them xenotransplantation of islet cells cultures.

It is possible that regeneration of beta-cells happens not only in the margins of localization of Langerhants islets but also in some structures outside of islet pancreatic tissue.

The invention will be illustrated in more detail with reference to the following Examples, but it should be understood that the present invention is not deemed to be limited thereto.

EXAMPLES

Example 1

At the initial stage of a real scientific-research work we used rats of Vistar line of body mass 220-250 grams received from a special nursery of lab animals as experimental animals. In order to eliminate hormonal cyclic influences on alteration of parameters of carbohydrate metabolism, we decided to carry on experiments on mature pubescent males.

In order to obtain objective results in conducting antidiabetic treatment in lab rates there was designed a model of a stable diabetes mellitus.

Disease in animals was provoked by introduction of fractional intraperitoneal administration of derivable extempore solution of Streptozotocin—total dose of 80 mg per 1 kg of body weight. Total of 90 animals were subjected to effect of streptozotocin. Later majority of animals developed characteristic signs of diabetic status: thirst, polyuria (excessive blood glucose), polyfagia (excessive food intake), hair fallout, slowing of body mass gain or its decline. At that, an expressed hyperglycemia was registered in 58 rats, i.e. other 22 retained normal glycemia or concentration of glucose rouse insignificantly. By the 4-week term after inducing of diabetes 32 animals with more stable level of hyperglycemia were picked over. Stability was confirmed by the fact that during almost a month-long observation, the concentration of blood sugar did not go lower than 16 mmol/l.

Choice of initial glycemia of such range is not on a chance basis as it is explained by the following. As previous experiments demonstrated, in glycemia of level of 16 mmol and higher, as registered in not less than in 4 weeks after administering Streptozotocinal, such rats do not demonstrate a spontaneous remission in the future as well as a reversion of a diabetic status. At the same time even a very high glycemia (still under 30 mmol/l) lets the majority of experimental animals with diabetes to survive for long periods (2 and more months), which allows conducting rather continuous experiments without any serious concerns for an untimely death of such animals. These assumptions were confirmed by observation over the control (no treatment) group of diabetic rats. Below are findings on an effect of intra-peritoneal xenotransplantation of cultures of islet cells of newborn rabbits on the course of Streptozotocinal Diabetes in 8 rats with consistent Streptozotocinal Diabetes Mellitus.

Each of animals-recipients, on the background of Hexenal intra-peritoneal narcosis, was administered 700,000-800,000 islet cells of pancreases of newborn rabbits by administration it through puncture in abdominal wall by a big diameter needle.

Below are findings regarding change in severity of diabetic status in each of 8 experimental animals of this group. The animals were divided in 3 groups of 8 rats each.

$1^{st}$ group: 8 rats with hyperglycemia, to whom xenotransplantation of cultures of islet cells into abdominal cavity was administered;

$2^{nd}$ group: 8 rats with hyperglycemia, to whom xenotransplantation of cultures of islet cells was administered into spleen pulp;

$3^{rd}$ group: 8 rats with hyperglycemia, who were not subjected to any treatment (control).

TABLE 3

Change of glycemia and body mass after application of Streptozotocin (Stz) and subsequent intraperitoneal transplantation (Tx) of islet cells cultures of pancreases of newborn rabbits in rat #1.

| Indexes | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 6.7 | 20.0 | 24.1 | 12.2 | 12.0 | 12.4 | 12.5 | 12.2 | 11.9 | 14.8 | 14.9 |
| Body Mass, g | 220 | 175 | 170 | 180 | 200 | 230 | | 250 | 290 | 330 | 340 |

TABLE 4

Change of glycemia and body mass after application of Streptozotocin (Stz) and subsequent intraperitoneal transplantation (Tx) of islet cells cultures of pancreases of newborn rabbits in rat #2.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 6.4 | 18.7 | 16.6 | 13.0 | 6.8 | 6.7 | 7.4 | 6.4 | 5.5 | 7.0 | 6.0 |
| Body Mass, g | 200 | 180 | 170 | 180 | 210 | 230 | 240 | 250 | 270 | 290 | 320 |

TABLE 5

Change of glycemia and body mass after application of Streptozotocin (Stz) and subsequent intraperitoneal transplantation (Tx) of islet cells cultures of pancreases of newborn rabbits in rat #3.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 5.4 | 26.8 | 29.0 | 16.1 | 22.2 | 16.5 | 12.5 | 14.1 | 17.7 | 16.5 | 15.9 |
| Body Mass, g | 200 | 180 | 160 | 160 | 170 | 200 | 210 | 220 | 240 | 250 | 290 |

TABLE 6

Change of glycemia and body mass after application of Streptozotocin (Stz) and subsequent intraperitoneal transplantation (Tx) of islet cells cultures of pancreases of newborn rabbits in rat #4.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 6.0 | 19.7 | 21.2 | 12.2 | 13.0 | 14.1 | 9.2 | 7.9 | 9.0 | 9.2 | 8.3 |
| Body Mass, g | 240 | 210 | 200 | 190 | 210 | 250 | 260 | 270 | 310 | 320 | 350 |

TABLE 7

Change of glycemia and body mass after application of Streptozotocin (Stz) and subsequent intraperitoneal transplantation (Tx) of islet cells cultures of pancreases of newborn rabbits in rat #5.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 4.9 | 18.9 | 17.9 | 15.5 | 15.9 | 14.0 | 15.9 | 15.0 | 15.2 | 16.8 | 14.6 |
| Body Mass, g | 200 | 180 | 170 | 180 | 200 | 220 | 240 | 250 | 270 | 280 | 300 |

TABLE 8

Change of glycemia and body mass after application of Streptozotocin (Stz) and subsequent intraperitoneal transplantation (Tx) of islet cells cultures of pancreases of newborn rabbits in rat #6.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 5.9 | 22.3 | 21.9 | 14.2 | 11.1 | 7.8 | 7.0 | 8.4 | 8.1 | 7.8 | 7.4 |
| Body Mass, g | 240 | 210 | 210 | 200 | 240 | 240 | 260 | 290 | 320 | 350 | 360 |

TABLE 9

Change of glycemia and body mass after application of Streptozotocin (Stz) and subsequent intraperitoneal transplantation (Tx) of islet cells cultures of pancreases of newborn rabbits in rat #7.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 5.9 | 18.0 | 17.1 | 11.5 | 7.9 | 8.1 | 6.4 | 5.4 | 6.1 | 5.1 | 6.4 |
| Body Mass, g | 200 | 180 | 170 | 180 | 200 | 220 | 240 | 250 | 270 | 280 | 300 |

TABLE 10

Change of glycemia and body mass after application of Streptozotocin (Stz) and subsequent intraperitoneal transplantation (Tx) of islet cells cultures of pancreases of newborn rabbits in rat #8.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 6.3 | 24.0 | 25.6 | 17.7 | 18.8 | 20.0 | 21.8 | 18.6 | 17.8 | 18.8 | 20.9 |
| Body Mass, g | 250 | 190 | 170 | 190 | 200 | 220 | 250 | 260 | 270 | 290 | 300 |

Example 2

Eight (8) rats with stable Streptozotocinal Diabetes Mellitus were subjected to intra-splenetic xenotransplantation of islet cells cultures. Administration of cultures of islet cells of pancreases of newborn rabbits was conducted on the background of Hexenal narcosis. After opening of an abdominal wall and bringing a spleen into an operative wound, a cellular suspension was introduced directly into the organ's pulp through the syringe of 1.2 mm in diameter. Place of injection was pressed with gauze tampon, by doing such slowing the parenchymal bleeding and sealing it by drops of special medical glue. Abdominal wall wound was stitched up layer by layer. Below are general results of such transplantations, exactly dynamics of indexes of glycemia and body mass of animals-recipients.

TABLE 11

Change of glycemia and body mass after application of Streptozotocin (Stz) and subsequent intra-splenetic transplantation (Tx) of islet cells cultures of pancreases of newborn rabbits in rat #17.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 5.3 | 16.7 | 17.1 | 16.8 | 12.2 | 10.2 | 10.0 | 11.2 | 9.9 | 8.1 | 6.6 |
| Body Mass, g | 220 | 200 | 200 | 190 | 200 | 240 | 250 | 280 | 320 | 340 | 360 |

TABLE 12

Change of glycemia and body mass after application of Streptozotocin (Stz) and subsequent intra-splenetic transplantation (Tx) of islet cells cultures of pancreases of newborn rabbits in rat #18.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 6.6 | 24.0 | 22.1 | 19.5 | 18.0 | 12.6 | 7.4 | 6.5 | 5.7 | 7.0 | 10.2 |

TABLE 12-continued

Change of glycemia and body mass after application of Streptozotocin (Stz) and subsequent intra-splenetic transplantation (Tx) of islet cells cultures of pancreases of newborn rabbits in rat #18.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Body Mass, g | 220 | 180 | 170 | 170 | 180 | 200 | 240 | 290 | 320 | 330 | 360 |

TABLE 13

Change of glycemia and body mass after application of Streptozotocin (Stz) and subsequent intra-splenetic transplantation (Tx) of islet cells cultures of pancreases of newborn rabbits in rat #19.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 5.3 | 21.2 | 21.2 | 17.6 | 14.4 | 10.5 | 11.2 | 11.4 | 9.1 | 10.5 | 7.4 |
| Body Mass, g | 250 | 220 | 210 | 190 | 200 | 210 | 250 | 270 | 300 | 310 | 350 |

TABLE 14

Change of glycemia and body mass after application of Streptozotocin (Stz) and subsequent intra-splenetic transplantation (Tx) of islet cells cultures of pancreases of newborn rabbits in rat #20.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 6.7 | 24.5 | 26.9 | 14.2 | 12.8 | 13.0 | 8.8 | 8.4 | 9.0 | 7.4 | 9.8 |
| Body Mass, g | 210 | 170 | 170 | 180 | 180 | 200 | 220 | 240 | 270 | 290 | 330 |

TABLE 15

Change of glycemia and body mass after application of Streptozotocin (Stz) and subsequent intra-splenetic transplantation (Tx) of islet cells cultures of pancreases of newborn rabbits in rat #21.

| Index | Prior to Stz | 4 weeks after Stz | Prior to Tx | Weeks | | | | | | | |
|---|---|---|---|---|---|---|---|---|---|---|---|
| | | | | 1 | 2 | 3 | 4 | 5 | 6 | 7 | 8 |
| Glycemia mM/l | 6.0 | 22.0 | 21.9 | 15.5 | 15.9 | 14.0 | 13.5 | 15.1 | 13.8 | 17.0 | 15.5 |
| Body Mass, g | 250 | 180 | 170 | 170 | 180 | 200 | 220 | 230 | 230 | 240 | 270 |

TABLE 16

Change of glycemia and body mass after application of Streptozotocin (Stz) and subsequent intra-splenetic transplantation (Tx) of islet cells cultures of pancreases of newborn rabbits in rat #22.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 7.1 | 31.4 | 28.8 | 24.2 | 25.9 | 22.7 | 17.0 | 17.9 | 18.1 | 16.7 | 15.8 |
| Body Mass, g | 220 | 170 | 170 | 160 | 160 | 180 | 200 | 220 | 230 | 250 | 270 |

TABLE 17

Change of glycemia and body mass after application of Streptozotocin (Stz) and subsequent intra-splenetic transplantation (Tx) of islet cells cultures of pancreases of newborn rabbits in rat #23.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 5.6 | 16.0 | 15.5 | 11.5 | 9.7 | 6.6 | 7.5 | 5.6 | 6.6 | 5.9 | 5.7 |
| Body Mass, g | 240 | 260 | 270 | 290 | 300 | 320 | 350 | 370 | 370 | 400 | 410 |

TABLE 18

Change of glycemia and body mass after application of Streptozotocin (Stz) and subsequent intra-splenetic transplantation (Tx) of islet cells cultures of pancreases of newborn rabbits in rat #24.

| Index | Prior to Stz | 4 weeks after Stz | Prior to Tx | Weeks 1 | 2 | 3 | 4 | 5 | 6 | 7 | 8 |
|---|---|---|---|---|---|---|---|---|---|---|---|
| Glycemia mM/l | 6.4 | 21.0 | 22.6 | 17.1 | 15.8 | 14.2 | 21.8 | 18.6 | 17.8 | 19.1 | 19.7 |
| Body Mass, g | 250 | 230 | 220 | 210 | 200 | 220 | 230 | 240 | 270 | 280 | 360 |

These data were later confirmed by observations over the control (diabetes without treatment) group of diabetic rats.

Example 3

26 animals were divided into 3 groups of 8 rats each: First group—8 rats with hyperglycemia subjected to xenotransplantation of islet cells culture through intraperitoneal administration. Second group—8 rats with hyperglycemia, which were subjected to xenotransplantation through intra-splenetic administration. Third group—10 rats with hyperglycemia, which were not treated at all (control). Greater number of such animals explained by projection of their possible death in the course of an experiment.

Below is data about an effect of intraperitoneal xenotransplantation of islet cells culture of newborn rabbits on the course of Streptozotocinal diabetes in 8 rats with expressed Streptozotocinal diabetes mellitus.

Each animal—recipient, on the background of Hexenal intraperitoneal narcosis, was introduced 700,000-800,000 of islet pancreas cells of newborn rabbits through puncture of peritoneum and release into abdominal cavity.

Below are findings on alterations of severity of diabetic status in each of the 8 rats of this group. Unlike rats with stable Streptozotocinal diabetes that were administered either intraperitoneal or intra-splenic transplantation of islet cells cultures of newborn rabbits, rats with the same severity of diabetic status that were not subjected to any treatment (control), level of glycemia remained stable high during the whole term of this experiment. In addition, no one rat-recipient died, but in a control group, on the background of a severe diabetic status 2 animals died, which makes it a ⅕ of animals of the group.

Below, are findings on alterations of glycemia level and body mass in rats with untreated experimental diabetes mellitus.

TABLE 19

Change of glycemia and body mass after application of Streptozotocin in rat #9 not subjected to transplantation (control).

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.4 | 25.8 | 23.9 | 23.4 | 26.6 | 24.7 | 23.3 | 24.4 | 22.6 | 24.3 |
| Body Mass, g | 250 | 230 | 210 | 200 | 200 | 180 | 170 | 170 | 180 | 180 |

TABLE 20

Change of glycemia and body mass after administering Streptozotocin in rat #10 not subjected to transplantation:

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 7.1 | 28.7 | 27.9 | >33 | 29.9 | 28.4 | >33 | 31.2 | e.l.* | |
| Body Mass, g | 200 | 180 | 170 | 160 | 160 | 150 | 150 | 130 | | |

*e.l. - exitus letalis

TABLE 21

Change in Glycemia and body mass after administering Streptozotocin to rat #11 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.4 | 26.8 | 24.9 | 23.4 | 26.6 | 25.7 | 27.3 | 24.9 | 25.5 | 23.7 |
| Body Mass, g | 220 | 220 | 210 | 200 | 190 | 180 | 170 | 180 | 180 | 180 |

TABLE 22

Change in Glycemia and body mass after administering Streptozotocin to rat #12 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.4 | 22.8 | 21.3 | 23.4 | 27.6 | 24.1 | 25.3 | 24.7 | 22.5 | 23.7 |
| Body Mass, g | 220 | 200 | 210 | 210 | 190 | 180 | 190 | 200 | 210 | 210 |

TABLE 23

Change in Glycemia and body mass after administering Streptozotocin to rat #13 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.4 | 21.8 | 23.0 | 23.7 | 24.6 | 23.6 | 28.3 | 24.8 | 25.0 | 23.8 |
| Body Mass, g | 220 | 240 | 230 | 220 | 210 | 200 | 190 | 180 | 190 | 200 |

TABLE 24

Change in Glycemia and body mass after administering Streptozotocin to rat #14 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 4.9 | 26.6 | 24.5 | 25.6 | 27.7 | 23.6 | 25.9 | 25.0 | 27.2 | 28.8 |
| Body Mass, g | 200 | 200 | 210 | 200 | 180 | 170 | 180 | 170 | 160 | 160 |

TABLE 25

Change in Glycemia and body mass after administering Streptozotocin to rat #15 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.9 | 19.4 | 19.5 | 19.6 | 20.0 | 18.7 | 18.7 | 19.7 | 19.7 | 20.3 |
| Body Mass, g | 200 | 220 | 210 | 200 | 210 | 210 | 210 | 220 | 220 | 230 |

TABLE 26

Change in Glycemia and body mass after administering Streptozotocin to rat #16 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.7 | 25.1 | 25.5 | 27.6 | 27.6 | 25.6 | 22.9 | 25.0 | 22.2 | 24.1 |
| Body Mass g | 230 | 220 | 210 | 200 | 190 | 200 | 190 | 180 | 180 | 180 |

TABLE 27

Change in Glycemia and body mass after administering Streptozotocin to rat #25 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 6.4 | 27.3 | 24.5 | 22.6 | 27.7 | 26.1 | 27.9 | e.i. | | |
| Body Mass, g | 210 | 220 | 200 | 190 | 190 | 180 | 180 | | | |

TABLE 28

Change in Glycemia and body mass after administering Streptozotocin to rat #26 not subjected to transplantation (control)

| Index | Prior to Stz | 4 weeks after Stz | Weeks | | | | | | | |
|---|---|---|---|---|---|---|---|---|---|---|
| | | | 1 | 2 | 3 | 4 | 5 | 6 | 7 | 8 |
| Glycemia mM/l | 5.8 | 17.7 | 17.3 | 18.3 | 22.9 | 21.3 | 19.9 | 18.3 | 19.7 | 17.7 |
| Body Mass, g | 230 | 250 | 260 | 260 | 250 | 270 | 280 | 280 | 280 | 300 |

Example 4

Cultures of Islet Cells

Cultures of islet cells were obtained in accordance of our designed technique from pancreases of 1-2 day newborn rabbits. For each transplantation, a culture containing approximately 200,000-300,000 beta-cells was used. Immediately before transplantation, culture was cleansed from previously added growth medium embryonic serum and collected it into sterile plastic test-tubes, each of 5 ml of volume. The attached fraction of a culture was removed with the help of special cellular scraper (firm Corning-Costar). The floating fraction was separated by centrifuging of culture broth that covered the bottle bottom where the attached fraction was located. Final volume of cellular suspension corresponded to the number of xenotransplantation operations scheduled for the day, and each milliliter of suspension should contain approximately 100,000 islet cells (generally beta-cells).

Example 5

Insulinotherapy

For subcutaneous injection we used specific action insulin Aktrapid HM that was administered twice a day: 9:00 and 19:00. Dose was selected individually. Criteria of successfulness of applied insulinotherapy was decreasing of hyperglycemia for up to 10 mmol/l and lower.

Example 6

Administering Islet Cells Cultures

Cellular suspension was injected by syringe through injection needle of big diameter, puncturing abdominal wall without anesthesia. To avoid injuries to internal organs and vessels of a rat, a rat was turned upside down, by that assuring anti-displacement of abdominal organs and formation of free space. After puncture of peritoneum the cellular transplant was injected into this free space.

Cavity operation is needed for intra-splenetic administration, so for narcosis by means of intraperitoneal injection we used prepared ex-tempore Hexenal solution based on ratio of 50-60 mg per 1 kg of body weight. Transplantation into spleen pulp was performed as follows: median incision along abdominal white line opened abdominal cavity. Spleen was drawn out into the operation wound surrounding it by sterile wipes. Cellular suspension collected the day before was drawn into syringe (2 ml volume) and through injection needle (0.5 mm diameter) administered into spleen pulp and into subcapsular zone. To avoid bleeding the injection mark was closed by medical glue MK-6.

Example 7

Laboratory Examination/Investigation

Capillary Blood Glucose was determined in experimental animals using Glucometr Smart Scan 2-3 times a week. Serum insulin was detected through immunoenzyme method, using sets for rabbit (human) insulin and custom-made sets for specific detection of rat insulin.

Example 8

Histological Research

For studying dynamics of morphological alterations happening in islets under influence of various types of treatment of experimental diabetes mellitus, pancreases of animals killed at the specified times during the experiment was fixated in freshly-made Buena mixture. After specific histological procedures (washing off fixative, dehydration, etc.) fragments of pancreatic tissue were sealed into paraffin. Then, made by microtome microscopic sections (5-7 mkm thick) were dewaxed and colored by hematoxilin and eosin as well as by aldehyde-fuchsine, for the purpose of isolation of beta-cells.

For detection of fate of beta-cells transplanted into spleen pulp of diabetic rats, during specified times after transplantation, dead animals' spleens and its fragments, which, judging from the scheme of the operation and some external signs, could, supposedly contain transplant, were exsected and immediately fixated in the Buena mixture. In succession as described above, paraffin sections were prepared and colored in specified manner.

Example 9

Research Results

Characteristics of Culture

Islet Cells cultures obtained for subsequent transplantation conformed to the accepted functional criteria. As such, studying under inverted microscope demonstrated that by the 2-week cultivation term the culture attained did not contain cells of exocrine tissue of pancreas that ballast cellular elements are absent including leukocytes—"passengers"—initiators of rejection of islet cells after its xenotransplantation. This data, and previous experience of transplantation treatment of experimental diabetes mellitus, assured us that there was no need for administering any type of immunosuppression. Control tests of insulin content in cultural broth demonstrated that existing beta-cells have high insulin-producing activity (Table 29).

TABLE 29

Indexes of basal and stimulated (25 mmol/l glucose) insulin secretion (concentration mkUNIT/ml) in islet cells culture produced from pancreases of newborn rabbits:

| Sample # | Basal | Stimulated |
|---|---|---|
| 1 | 2360 | 3330 |
| 2 | 11080 | 13450 |
| 3 | 7800 | 8760 |
| 4 | 5580 | 7650 |
| 5 | 7530 | 9900 |
| 6 | 8800 | 12300 |
| 7 | 5090 | 6850 |

Example 10

Results of Insulin Therapy

As it was stated in previous works, selection of effective doses of insulin in treatment rats with experimentally induced Streptozotocin induced diabetes mellitus is a difficult, lengthy (sometimes practically endless) and ungrateful work. Insulin-resistance often revealed in that. However, in majority of animals of the $1^{st}$ test group (5 out of 8) we succeeded by means of high doses of insulin to lower hyperglycemia up to levels of less than 10 mmol/l and to maintain such compensation of impairment of carbohydrate metabolism during the 8-week period (tab.30).

TABLE 30

Changes in Glycemia in rats with experimentally induced diabetes mellitus ($1^{st}$ group) under the influence of daily insulin therapy.

| ## | Length of insulin therapy (days) | | | | | | | | | |
|---|---|---|---|---|---|---|---|---|---|---|
| RAT | 0 | 7 | 13 | 21 | 28 | 35 | 41 | 46 | 53 | 60 |
| 9 | 17.7 | 15.5 | 12.1 | 10.8 | 11.9 | 10.0 | 7.9 | 8.5 | 6.7 | 6.4 |
| 10 | 28.7 | 29.0 | 26.7 | 22.4 | 27.8 | 23.3 | 22.8 | 24.9 | 15.5 | 18.4 |
| 11 | 18.6 | 18.9 | 15.9 | 11.0 | 9.7 | 12.3 | 11.5 | 8.6 | 10.6 | 9.7 |
| 12 | 16.1 | 12.0 | 11.1 | 8.7 | 6.7 | 5.4 | 6.6 | 8.1 | 6.3 | 6.3 |
| 13 | 29.7 | 26.7 | 22.8 | 13.4 | 14.5 | 16.9 | 18.5 | 14.6 | 20.3 | 18.8 |
| 14 | 24.4 | 22.2 | 18.0 | 22.1 | 18.3 | 19.1 | 17.7 | 14.8 | 18.8 | 14.3 |
| 15 | 19.0 | 18.7 | 14.3 | 11.2 | 8.6 | 9.9 | 10.8 | 8.6 | 9.9 | 7.7 |
| 16 | 24.2 | 18.8 | 13.8 | 9.9 | 12.0 | 10.2 | 9.7 | 6.7 | 8.6 | 8.9 |
| Average dose (unit) of insulin | 0 | 4 | 8 | 12 | 16 | 14.1 | 12.8 | 17.6 | 11.9 | 13.3 |

Although we succeeded in lowering level of glycemia in rats #10, 13 and 14, lack of adequate reaction in response to introduction of immense doses of insulin (up to 20-30 units per day) did not allow us to reveal tendency to normalization of glycemia and to admit presence in these animals of high individual insulin-resistance; and possibility for significant regeneration of own islet apparatus would be unlikely, all the more so that after stopping administration of insulin all rats from the $1^{st}$ group had quick recurrence of hyperglycemia close to initial level.

Example 11

Results of Xenotransplantation of Cultures of Islet Cells

Expressed anti-diabetic effect of xenotransplantation of cultures of islet cells was noted both in cases of injection of transplant into peritoneum ($2^{nd}$ group of experimental rats), and in its introduction into spleen pulp ($3^{rd}$ group). Effect is seen in decreasing of clinical manifestation of diabetic status and also in expressed depletion of level of hyperglycemia. As data presented in tables shows, character of depletion of glycemia in the course of both methods of administering of xenotransplant is, to some extent, different from each other. These differences comprise as in term of manifest of sugar-lowering effect, its severity, and in its persistence (stability).

TABLE 31

Changes of glycemia in rats with experimental diabetes mellitus after intraperitoneal xenotransplantation of cultures of islet cells ($2^{nd}$ group)

| Rat # | Before trans- plantation | Days after transplantation | | | | | | | |
|---|---|---|---|---|---|---|---|---|---|
| | | 2 | 7 | 10 | 13 | 15 | 17 | 20 | 22 |
| 1 | 24.1 | 18.7 | 12.2 | 15.5 | 12.0 | 11.9 | 14.5 | 12.4 | 14.8 |
| 2 | 16.6 | 15.0 | 13.0 | 8.8 | 6.8 | 9.0 | 7.7 | 6.7 | 9.1 |
| 3 | 29.0 | 27.9 | 16.1 | 17.7 | 22.2 | 18.4 | 15.5 | 14.1 | 16.5 |
| 4 | 21.2 | 18.8 | 12.2 | 13.0 | 13.0 | 11.0 | 12.2 | 10.5 | 8.9 |
| 5 | 17.9 | 14.8 | 15.5 | 16.8 | 15.9 | 16.0 | 15.9 | 14.0 | 13.7 |
| 6 | 21.9 | 19.1 | 14.2 | 12.8 | 11.1 | 8.5 | 9.0 | 7.8 | 7.1 |
| 7 | 17.1 | 16.6 | 11.4 | 9.8 | 7.0 | 7.9 | 6.4 | 8.1 | 8.6 |

TABLE 31-continued

Changes of glycemia in rats with experimental diabetes mellitus after intraperitoneal xenotransplantation of cultures of islet cells ($2^{nd}$ group)

| Rat # | Before trans- plantation | Days after transplantation | | | | | | | |
|---|---|---|---|---|---|---|---|---|---|
| | | 2 | 7 | 10 | 13 | 15 | 17 | 20 | 22 |
| 8 | 25.6 | 21.1 | 17.7 | 17.1 | 18.8 | 20.7 | 18.6 | 21.2 | 20.0 |
| M | 21.7 | 19.0 | 14.1 | 13.9 | 13.3 | 12.9 | 12.3 | 11.9 | 12.3 |

TABLE 32

Changes of glycemia in rats with experimental diabetes mellitus after intraperitoneal xenotransplantation of cultures of islet cells (2$^{nd}$ group) - continued

| Rat # | Days after transplantation | | | | | | | | |
|---|---|---|---|---|---|---|---|---|---|
|  | 24 | 26 | 28 | 30 | 32 | 35 | 37 | 40 | 42 |
| 1 | 13.2 | 13.9 | 12.5 | 14.4 | 16.8 | 12.2 | 15.5 | 12.0 | 11.9 |
| 2 | 7.8 | 7.0 | 7.4 | 6.7 | 5.5 | 6.4 | 6.4 | 5.9 | 5.5 |
| 3 | 17.2 | 14.8 | 12.5 | 14.7 | 15.6 | 14.1 | 16.5 | 16.1 | 17.7 |
| 4 | 10 | 10.1 | 9.2 | 10.5 | 8.4 | 7.9 | 11.1 | 8.7 | 9.0 |
| 5 | 13.9 | 14 | 15.9 | 12.4 | 14.7 | 15.0 | 14.3 | 13.8 | 15.2 |
| 6 | 8.1 | 8.0 | 7.0 | 6.7 | 7.1 | 8.4 | 9.0 | 7.8 | 8.1 |
| 7 | 8.7 | 7.4 | 6.4 | 5.1 | 6.5 | 5.6 | 4.9 | 5.8 | 6.1 |
| 8 | 18.8 | 20.6 | 21.8 | 22.2 | 19.2 | 18.6 | 21.2 | 20.0 | 17.8 |
| M | 11.9 | 12.0 | 11.6 | 11.6 | 11.7 | 11.0 | 12.4 | 11.3 | 11.4 |

TABLE 33

Changes of glycemia in rats with experimental diabetes mellitus after intraperitoneal xenotransplantation of cultures of islet cells (2$^{nd}$ group)

| Rat # | Days after transplantation | | | | | | | |
|---|---|---|---|---|---|---|---|---|
|  | 44 | 46 | 49 | 51 | 53 | 55 | 57 | 60 |
| 1 | 12.5 | 14.4 | 16.8 | 18.2 | 17.5 | 16.7 | 15.6 | 14.9 |
| 2 | 6.7 | 5.5 | 7.0 | 7.4 | 6.7 | 6.8 | 6.0 | 5.7 |
| 3 | 15.5 | 14.1 | 16.5 | 16.8 | 15.9 | 17.7 | 15.9 | 16.0 |
| 4 | 10.0 | 11.0 | 9.2 | 10.5 | 8.9 | 7.9 | 8.3 | 9.4 |
| 5 | 14.8 | 15.5 | 16.8 | 15.9 | 16.0 | 14.6 | 15.7 | 17.0 |
| 6 | 8.5 | 8.0 | 7.8 | 7.1 | 6.7 | 7.4 | 6.4 | 5.1 |
| 7 | 7.1 | 6.6 | 5.1 | 6.8 | 7.0 | 7.9 | 6.4 | 5.1 |
| 8 | 17.7 | 17.1 | 18.8 | 21.9 | 19.1 | 21.0 | 20.9 | 17.8 |
| M | 11.6 | 11.5 | 12.3 | 13.1 | 12.2 | 12.5 | 11.9 | 11.4 |

After analyzing the obtained results of measuring glycemia in rats with experimental diabetes mellitus in which an intraperitoneal xenotransplantation of cultures of islet cells was performed, it is possible to made a conclusion of achieving expressed anti-diabetic effect in majority of animals-recipients.

As such, rats #2, 4, 6, and 7 had remission of the diseases manifested in stabilization of blood sugar at a normal or almost normal level.

Rats #1 and 3 demonstrated not so intensive decrease in glycemia level, although statistical data is very reliable. In such cases we may only talk about fractional remission of hypoglycemic status, all the more so that rat #1 during the last weeks of observation revealed a tendency of growing of previously moderate hyperglycemia.

In other animals (rats ##5 and 8) decline of glycemia was not significant and not stable, which fact bears evidence of a failure of these two transplantations of cultures of islet cells.

TABLE 34

Changes of glycemia in rats with experimental diabetes mellitus after intra-splenetic xenotransplantation of cultures of islet cells (3$^{rd}$ group)

| Rat # | Before trans- plantation | Days after transplantation | | | | | | | |
|---|---|---|---|---|---|---|---|---|---|
|  |  | 2 | 7 | 10 | 13 | 15 | 17 | 20 | 22 |
| 17 | 17.1 | 15.5 | 16.8 | 13.5 | 12.2 | 9.9 | 12.4 | 10.2 | 9.4 |
| 18 | 22.1 | 21.0 | 19.5 | 17.8 | 18.0 | 15.6 | 17.1 | 12.6 | 12.1 |
| 19 | 21.2 | 21.9 | 17.6 | 18.7 | 16.2 | 14.4 | 11.8 | 12.2 | 10.5 |
| 20 | 26.9 | 21.8 | 14.2 | 13.0 | 12.8 | 11.8 | 12.2 | 10.5 | 13.0 |
| 21 | 21.9 | 14.8 | 15.5 | 14.1 | 15.9 | 13.6 | 15.5 | 14.0 | 13.3 |
| 22 | 28.8 | 29.1 | 24.2 | 30.8 | 25.9 | 21.8 | 25.2 | 27.1 | 22.7 |
| 23 | 15.5 | 13.6 | 11.5 | 8.8 | 9.0 | 9.7 | 7.4 | 8.0 | 6.6 |
| 24 | 22.6 | 23.1 | 17.1 | 14.7 | 15.8 | 12.2 | 15.5 | 12.0 | 14.2 |
| M | 19.3 | 20.1 | 17.1 | 16.2 | 15.2 | 13.6 | 14.0 | 13.3 | 12.5 |

TABLE 35

Changes of glycemia in rats with experimental diabetes mellitus after intra-splenetic xenotransplantation of cultures of islet cells (3$^{rd}$ group) - continued

| Rat # | Days after transplantation | | | | | | | | |
|---|---|---|---|---|---|---|---|---|---|
|  | 24 | 26 | 28 | 30 | 32 | 35 | 37 | 40 | 42 |
| 17 | 10.2 | 10.9 | 10.0 | 9.4 | 8.7 | 11.2 | 10.5 | 9.8 | 9.9 |
| 18 | 11.8 | 8.7 | 7.4 | 6.4 | 5.1 | 6.5 | 6.6 | 7.9 | 5.7 |
| 19 | 17.7 | 16.8 | 11.2 | 14.0 | 10.6 | 11.4 | 10.6 | 11.1 | 9.1 |
| 20 | 8.4 | 9.0 | 8.8 | 8.7 | 7.5 | 8.4 | 9.0 | 9.7 | 9.0 |
| 21 | 15.9 | 12.4 | 13.5 | 12.4 | 14.0 | 15.1 | 13.4 | 13.8 | 12.8 |
| 22 | 18.1 | 18.0 | 17.0 | 18.1 | 18.4 | 17.9 | 18.1 | 17.8 | 18.1 |
| 23 | 9.7 | 7.4 | 7.5 | 6.5 | 5.4 | 5.6 | 5.4 | 5.8 | 6.6 |
| 24 | 18.8 | 20.6 | 21.8 | 22.2 | 19.2 | 18.6 | 21.2 | 20.0 | 17.8 |
| M | 13.8 | 12.1 | 12.2 | 12.2 | 11.1 | 11.8 | 11.9 | 12.0 | 11.1 |

| Rat # | Days after transplantation | | | | | | | |
|---|---|---|---|---|---|---|---|---|
|  | 44 | 46 | 49 | 51 | 53 | 55 | 57 | 60 |
| 17 | 11.5 | 10.4 | 8.1 | 8.2 | 8.7 | 6.7 | 6.6 | 4.9 |
| 18 | 6.7 | 5.5 | 7.0 | 7.4 | 9.2 | 10.5 | 8.9 | 7.9 |
| 19 | 10.5 | 9.4 | 10.5 | 8.8 | 9.9 | 7.4 | 8.9 | 9.1 |
| 20 | 9.1 | 6.7 | 7.4 | 7.1 | 11.0 | 7.8 | 9.8 | 7.5 |
| 21 | 14.8 | 15.7 | 17.0 | 15.9 | 13.6 | 14.0 | 15.5 | 16.8 |
| 22 | 17.5 | 17.8 | 16.7 | 16.8 | 16.0 | 15.7 | 14.9 | 15.8 |
| 23 | 8.7 | 6.0 | 5.9 | 8.3 | 7.6 | 6.7 | 4.6 | 5.7 |
| 24 | 21.5 | 21.1 | 19.1 | 21.0 | 18.8 | 21.0 | 18.9 | 19.7 |
| M | 12.5 | 10.3 | 11.5 | 11.7 | 11.9 | 11.2 | 11.0 | 10.9 |

After xenotransplantation of islet cells culture into pulp of a spleen, expressed digression of hyperglycemia was noted in majority of animals (7 out of 8). At that, practical normalization of glycemia happened in 5 rats with experimental diabetes mellitus (##17-20, 23). Also, in one additional recipient (rat #21) level of blood glucose depleted significantly, but its level remained at average hyperglycemic level, and in the second half of the term of observation gradual increase of glycemia was noted, which may be even evaluated as a definite recurrence of high hyperglycemia. In two of the group's animals (#22 and 24) there was no ample anti-diabetic effect achieved, although rat #22 reached statistically reliable decrease of glycemia, but it cannot be classified as a remission of diabetes.

As it was previously noted, we expect divergence in glycemia changes in comparison between intraperitoneal and intra-splenetic methods of xenotransplantation, but it appeared not be very fundamental. For the purpose of simplicity of comparison, we combined glycemia indicators in 2$^{nd}$ and 3$^{rd}$ group of animals in dynamics into one table (#34).

TABLE 36

Dynamics of changes in glycemia (average, M) in rats of the $2^{nd}$ group (intraperitoneal xenotransplantation) and in $3^{rd}$ group (intra-splenetic transplantation) in rats - recipients:

| Group # | Prior to transplantation | Days after transplantation | | | | | | | |
|---|---|---|---|---|---|---|---|---|---|
| | | 2 | 7 | 10 | 13 | 15 | 17 | 20 | 22 |
| $2^{nd}$ | 21.7 | 19.0 | 14.1 | 13.9 | 13.3 | 12.9 | 12.3 | 11.9 | 12.3 |
| $3^{rd}$ | 19.3 | 20.1 | 17.1 | 16.2 | 15.2 | 13.6 | 14.0 | 13.3 | 12.5 |

| Group # | Days after transplantation | | | | | | | | |
|---|---|---|---|---|---|---|---|---|---|
| | 24 | 26 | 28 | 30 | 32 | 35 | 37 | 40 | 42 |
| $2^{nd}$ | 11.9 | 12.0 | 11.6 | 11.6 | 11.7 | 11.0 | 12.4 | 11.3 | 11.4 |
| 3rd | 13.8 | 12.1 | 12.2 | 12.2 | 11.1 | 11.8 | 11.9 | 12.0 | 11.1 |

| Group # | Days after transplantation | | | | | | | |
|---|---|---|---|---|---|---|---|---|
| | 44 | 46 | 49 | 51 | 53 | 55 | 57 | 60 |
| $2^{nd}$ | 11.6 | 11.5 | 12.3 | 13.1 | 12.2 | 12.5 | 11.9 | 11.4 |
| $3^{rd}$ | 12.5 | 10.3 | 11.5 | 11.7 | 11.9 | 11.2 | 11.0 | 10.9 |

Subsequent to the completion of physiological portion of research, animals enacted in this experiment, were put to death painlessly. At that, blood samples were taken from experimental animals, and processed serum was tested for insulin (also rabbit's, and rat's). Shown below are results of immunoenzyme analysis (enzyme immunoassay) of samples of rats-recipients' blood serum, which analyses were performed utilizing various special sets. (Table 35).

TABLE 37

Content of xenogenous (rabbit) and own insulin in blood serum of rats subjected to transplantation of cultures of islet cells of pancreases of newly-born rabbits:

| Rat # | Rabbit Insulin; | Rat Insulin | Total Insulin |
|---|---|---|---|
| 1 | 16 | 7 | 23 |
| 2 | 16 | 52 | 68 |
| 3 | 45 | 11 | 56 |
| 4 | 23 | 50 | 73 |
| 5* | — | — | — |
| 6 | 57 | 53 | 110 |
| 7 | 21 | 48 | 69 |
| 8 | 9 | 20 | 29 |
| 17 | 23 | 60 | 83 |
| 18* | — | — | — |
| 19 | 17 | 134 | 151 |
| 20* | — | — | — |
| 21 | 4 | 24 | 28 |
| 22 | 6 | 27 | 33 |
| 23 | 5 | 74 | 79 |
| 24 | 0 | 7 | 7 |

*no verifiable result due to intensive hemolysis (mass erythrocyte lysis) of serum. In addition, we analyzed blood samples obtained after completion of experiments from rats with Streptozotocinal diabetes, who had been subjected to insulin therapy In this, serum was examined for human and rat insulin content (tab.36) with utilization corresponding sets for immunoenzyme analysis.

TABLE 38

Content of human and rat insulin in blood serum of rats subjected to insulin therapy ($1^{st}$ group).

| Rat # | Human Insulin | Rat insulin | Total insulin |
|---|---|---|---|
| 9 | 194 | 17 | 211 |
| 10* | — | — | — |
| 11 | 258 | 24 | 282 |
| 12 | 79 | 23 | 102 |
| 13 | 144 | 0 | 144 |
| 14 | 331 | 4 | 335 |
| 15* | — | — | — |
| 16 | 261 | 0 | 261 |

*verifiable result was not obtained due to intensive hemolysis

It is not simple to interpret the obtained results. Complexity of analysis is conditioned, first of all, by the fact that demonstrated in tables data reflects, in particular, an insulin-producing function of xenotransplanted rabbit beta-cells and own (rat) beta-cells (Tab.8), or of injected human insulin and own rat insulin (Tab.9) only at the moment of completion of multi-day experiment. Certainly, it would be great to have data about dynamics of content of varied types of insulin in varied terms during the experiments. But extreme difficulty of getting non-hemolyzed blood from small lab animals in quantities adequate for preparation of needed volume of serum without causing serious trauma to animals, does not allow implementing it without risk of loosing such valuable lab animals. So, we would be acting on the basis of the data that we have available.

It appears that in majority of cases (11 out of 13) rabbit insulin was detected in blood of rats-recipients, which is an unchallengeable evidence of presence in animals' blood of rabbit 9 i.e. xenotransplanted beta-cells secreting into "new owner's" blood an insulin relevant to a donor. Its concentration fluctuates significantly from 4 to 57 pmol/l.

Segment of rat-recipients in which their own species insulin was detected is even more (12 out of 13). Fluctuations of its content are very large—from 7 to 134 pmol/l. Distinctive from interpretation of presence of xenogeneic insulin in animals subjected to xenotransplantation of islet cells, it is impossible to give a single-value estimate to the detection of one or the other concentrations of insulin secreted by beta-cells of lab rats with experimental diabetes. It is possible to evaluate more or less objectively to obtained data, when considering proportion of several interrelated quantitative data, namely: interconnection of glycemia level and of total insulinemia, ratio of rat and rabbit insulin (in rats-recipients) or human insulin (in rats subjected to injection of its preparation), and also to try to correlate dynamics of glycemia from start to finish of observation with different (in species (specific) origin) insulinemia.

An analysis was conducted in selective, but characterizing for common consistent patterns, order, various correlations of glycemia indicators and concentration of insulin in lab animals' blood serum were reviewed. From each group 3 rats were selected with more representative results of lab exams, and will tabulate all data in one table (Tab. #37).

TABLE 39

Indicators of glycemia and insulinemia in some rats of the $2^{nd}$, $3^{rd}$ and $1^{st}$ group of experimental rats with experimental diabetes mellitus.

| Rat ## | Initial glycemia mmol/l | Final glycemia mmol/l | Rabbit (human) insulin pmol/l | Rat insulin pmol/l | Total insulin pmol/l |
|---|---|---|---|---|---|
| 2 | 16.6 | 5.7 | 16 | 52 | 68 |
| 4 | 21.2 | 9.4 | 23 | 50 | 73 |

TABLE 39-continued

Indicators of glycemia and insulinemia in some rats of the $2^{nd}$, $3^{rd}$ and $1^{st}$ group of experimental rats with experimental diabetes mellitus.

| Rat ## | Initial glycemia mmol/l | Final glycemia mmol/l | Rabbit (human) insulin pmol/l | Rat insulin pmol/l | Total insulin pmol/l |
|---|---|---|---|---|---|
| 8 | 25.6 | 17.8 | 9 | 20 | 29 |
| 17 | 17.1 | 4.9 | 23 | 60 | 83 |
| 19 | 21.2 | 9.1 | 17 | 134 | 151 |
| 24 | 22.6 | 19.7 | 0 | 7 | 7 |
| 9 | 17.7 | 6.4 | 194 | 17 | 211 |
| 14 | 24.4 | 14.3 | 331 | 4 | 335 |
| 16 | 24.2 | 8.9 | 261 | 0 | 261 |

The analysis of results drawn in the $2^{nd}$ experimental group (xenotransplantation of cultures of islet cells into peritoneum) was done. In both successful cases (rats #2 and #4), remission of diabetic status was accompanied by significant decrease of glycemia—from 16.6 & 21.2 mmol/l to 5.7 & 9.4 mmol/l respectively. At that, at the very end of 2-month observation normalization of levels of insulinemia (respectively up to 68 and 73 pmol/l) mainly on account of restoration of insulin-producing activities of own beta-cells of rats-recipients (52 & 50 pmol/l respectively), although share of insulin secreted by xenotransplanted beta-cells of newly-born rabbits appears to be relatively sufficient (16 & 23 pmol/l respectively). The third animal of that group (rat #8) with initially higher level of hyperglycemia (25.6 pmol/l), demonstrated functioning of transplanted beta-cells (rabbit insulin concentration 9 pmol/l) along with own beta-cells (concentration of rat insulin—20 pmol/l). Total (basically on account of own efforts of islets of recipient's pancreas) insulin production secured statistically meaningful drop in hyperglycemia (up to 17.8 pmol/l), however, it was not enough for achieving remission of diabetic status.

In the $3^{rd}$ experimental group (intra-splenetic xenotransplantation of islet cells) rats ##17 and 19 were chosen as examples, they had initial and final glycemia very similar to same in rats ##2 and 4 from the 2nd group. However, if data on glycemia and insulinemia in rats #2 and 17 appeared to be very close (respectively: initial glycemia 16.6 & 17.1 mmol/l, ending glycemia—5.7 & 4.9 mmol/l, rat insulin—52 & 60 p/mol/l), then in rats #4 and #19 upon identity of initial glycemia (21.2 & 21.2 mmol/l) and similarity of ending glycemia (9.4 & 9.1 mmol/l), the total insulinemia happened to be very distinctive (more than 2 time—respectively 73 and 151 pmol/l). At such, this distinction was, in general, due to differences in concentration of rat insulin (respectively 50 & 134 pmol/l).

In rats of the first group, due to super-intensive insulinotherapy, it was possible to achieve normal or close to normal content of glucose in blood. Apparently, due to restoration of applicable disturbed metabolism, conditions for partial restoration of pool of own beta-cells of experimental animals emerged. However, the degree of achieved regeneration appeared to be deficient for this amount of regenerated beta-cells to produce quantities of insulin sufficient to affect significantly the development of experimental diabetes mellitus.

In some rats that were subjected to xenotransplantation of islet cells cultures and that demonstrated remission of diabetic status, only partial regeneration of beta-cells was noted (picture 6). However, anti-diabetic effect was, probably, provided by insulin-producing activity of beta-cells of newborn rabbits successfully transplanted into rats-recipients. This is indicated by findings of research of content of xenogenous (rabbit's) and own (rat's) insulin in blood. (table 8).

Research of pancreases of rats with experimental Diabetes Mellitus, in which significant anti-diabetic effect after xenotransplantation of islet cell cultures of newborn rabbits was noted, revealed regeneration of beta-cells. In such, the stated restorative process was noted, as a rule, exactly in Langerhants islets, precisely in places of their localization.

Special coloring of tissue of pancreas of rats-recipients subjected to a successful xenotransplantation of islet cells cultures demonstrated that regeneration of structures of Langerhants islets happened, generally, on account of beta-cells. At the same time the appearance of single point beta-cells (colored by Aldehyde-fuchsin) is noted outside of islet localization, which can indirectly indicate a possibility of generation of beta-cells out of out-of-islet structures, probably, duct epithelium.

Accordingly, based on results of conducted scientific experiments, it is possible to make several general conclusions:

Streptozotocin causes general destructing effect on beta-cells of pancreatic islet cells, but at the same time, directly or indirectly, leads to the loss of other cells.

It appears that regenerative process in affected Langerhants islets happens, mainly, due to restoration of beta-cells pool.

Intensive insulinotherapy is not capable only due to normalization of glycemic status to provide decently expressed rehabilitation process in pancreatic islets of rats with Streptozotocinal Diabetes Mellitus.

Islet cells cultures produced from pancreases of newborn rabbits utilizing an original method, consist, principally, of beta-cells purified from ballast cellular elements and have a very high insulin-producing activity.

Both intra-peritoneal and intra-splenetic xenotransplantation of islet cells cultures to rats with experimental Streptozotocinal Diabetes Mellitus, in majority of cases, secures stable remission of diabetic status during at least 8 weeks.

Post-transplantation sugar-reducing effect is assured both, by functioning of transplanted beta-cells and by insulin-producing activity of to some degree restored pool of beta-cells in islets of pancreases of rats-recipients. This is supported by findings on fluctuations of concentrations of exogenous (rabbits') and own (rats') insulin in blood of experimental animals.

Histological examinations of pancreases of experimental rats confirmed insignificant role of intensive insulin-therapy and expressed stimulation of regenerative processes in islets of rats with Streptozotocinal Diabetes Mellitus after xenotransplantation of islet cells cultures.

Possibly, regeneration of beta-cells happens not only in the borders of localization of Langerhants islets, but also in certain structures of out-of islet pancreatic tissue.

It is difficult to give interpretation of these results. Only one working version can be advanced—presence of decreased sensitivity of insulin receptors in rat #19 towards own insulin. Insignificant decrease of hyperglycemia in rat #24 can be explained by lack, apparently, of unsettled (or rejected due to immunologic incompatibility, or disposed of its insulin-producing activity as a result of phenomenon of apoptosis) xenotransplanted beta-cells (rabbit insulin—0) and weak hormonal activity of own beta-cells of the animal (rat insulin—7 pmol/l).

Exactly the above stated reduced sensitivity of insulin receptors (but exactly towards introduced from outside (synthesized human insulin) can explain very high levels insulinemia (respectively 194, 331 and 261 pmol/l) in rats of the $1^{st}$ group (##9, 14 & 16) who had been subjected to daily insulin therapy. At that, concentration of own insulin in these animals was low (in rats 9 and 14) or even not detected at all. (rat #16).

It is a possibility, that presence in the blood of large amounts of exogenous insulin prevented more significant activity of own beta-cells of islets of pancreas of rats of the $1^{st}$ group. High concentration of exogenous insulin, due to feedback rule, facilitated peculiar atrophy of islets apparatus "disuse atrophy". Not excluding that on the background of super-intensive insulin therapy, whose regime cannot compete with normal secretion of insulin by healthy endocrine pancreas, rats demonstrated expressed hypoglycemic episodes, which were curtailed by excessive food intake (feeding was unlimited), which in itself increased requirements in administered insulin. We shall consider, naturally, pro-diabetic impact of whole group of hormones which concentration is sharply increased in the process of development of hypoglycemic status, and an impact of variety of stress-inducing situations, such as blood taking, operative interventions, and etc.

In contrast with intensive insulin therapy, more exact—hyper-insulin-therapy, anti-diabetic effect of xenotrasplantation of cultures of islet cells rides by secretion into animals-recipients' blood of amounts of insulin being secreted by transplanted beta-cells more or less adequate to level of glycemia. In addition, secretion of insulin happens in abdominal cavity or in the spleen, resulting in hormone getting into system of portal vein, which can be considered as practically physiological, i.e. natural way for organism.

Successful experimental researches that demonstrated high anti-diabetic effect of grafting of islet cells obtained from pancreases of newborn rabbits, allowed to use such cultures in clinical practice.

Example 12

Intramuscular Xenotransplantations of Cultures of Islet Cells

Total of 112 patients with diabetes mellitus of type 1 were under well-documented dynamic observation. Of 112 patients, there were 58 men, and 54 women. Patients' age at the moment of transplantation was from 16 to 53—average 33.5 years old.

It is known that severity of manifestation of secondary diabetic complications depends significantly on longevity of the disease. Supposedly, destruction of own beta-cells of the patient as a result of autoimmune process approximately happens on the $5^{th}$ year after manifestation of the disease. Secondary diabetic complications manifest itself usually in patients with longevity of disease of more than 10 years. Because of that, all patients were divided in 3 groups in reference to longevity of the disease: a.) 1 to 5 years—16 people; b.) 6 to 10 years—43 people, c.) more than 10 years—53 patients. All patients had been examined to determine character of development of Diabetes mellitus and establishing presence of diabetic complications.

Usually, Islet Cells cultures received through the above-described methods out of 50-60 pancreases of 1-2 day newborn rabbits were used for transplantation dose for 1 patient.

Each dose of the culture contained 1.5-2.0 mln of beta-cells. Collected immediately prior to transplantation islet cells cultures were injected through the syringe into muscles recti abdominis under local anesthesia. No immune suppression was used.

Below is the description of technique of transplantation of cultures of islet cells.

One dose of cultures of islet cells represents a sterile suspension in Hank's salt solution (10-15 ml volume) placed in a plastic tube marked in an appropriate way. Using an injection needle of not less than 7 cm in length and more than 1 mm in diameter, the islet cell suspension is collected into a syringe of 20 ml in volume.

On the right side of the patients' umbilicus in the projection zone of musculus abdominis rectus utilizing separate syringe and corresponding injection needle the local infiltration anesthesia of frontal abdominal wall (by Novocain or other anesthetic) is performed.

After anesthesia we use injection needle to perform puncture of sub-aponeurosis space of the musculus abdominis rectus, and suspension of cultures of islet cells The place of injection is to be closed by a sterile bandage.

In addition to traditional administering of Islet cells cultures into transverse abdominal muscle, a more complex but more physiological method of transplantation has found its application—transplantation through the portal vein, access to which is actualized through bougienage of obliterated umbilical vein. There are some grounds to consider (almost 20 of such transplantations were fully analyzed) that due to this method of administration, the quicker and more expressed sugar-reducing action of transplantation is achieved, as well as significant reduction of requirements in exogenous insulin. (Shumakov et al., 1993 {16}.) However, the degree of therapeutic effect of intra-portal transplantation of cultures of islet cells of pancreases of newborn rabbits on secondary diabetic complications is practically indistinctive from effects of intramuscular transplantation. Because of specific technical complexities and possible surgical risks of this method, it has been abandoned, and almost all transplantations are performed utilizing a safe and simple method of injection cell suspension under the aponeurosis of transverse abdominal muscle.

At the same time, while performing series of intraportal transplantations, we examined an ability of beta-cells containing in cultures of islet cells of newborn rabbits to respond to corresponding stimulus by secretion in-vivo—i.e. in an organism of a type-1 diabetes patient. Five male patients were subjected to this research, their age varied from 25 to 45 years, history of disease—from 12 to 25 years. Along the guide, control of X-ray screen televisual apparatus, through the left subclavicular vein the catheter was placed in the right hepatic vein. Blood intake (5 ml) was performed instantaneously out of hepatic and portal veins (through trans-umbilical catheter that had been placed during the prior transplantation of islet cells culture. After that, for the purpose of local stimulation of intraportally transplanted islet cells cultures of pancreases of newborn rabbits, some 20 ml of 20%-glucose solution was injected into portal vein, in analogue with a rate of 1 gram of glucose per 1 kilogram of patient's body weight, which had been used in intravenous load test. Blood draft from portal and hepatic veins was done in 1 min, in 5 min, in 15 min, in 30 min, and in 60 minutes after administration of glucose. As blood exam for insulin content showed, prior to stimulation, there was already a difference between insulin concentrations in portal vein and in hepatic vein (respectively $4.9 \pm 0.6$ and $6.1 \pm 1.0$ mkUNIT/ml). In 1 minute after glucose administration insulin concentration was noted to increase 1.5 times in hepatic vein (from $6.1 \pm 1.0$ to $9.1 \pm 1.3$ mkUNIT/ml; $p<0.05$), which is twice as large than its concentration in portal vein (4.2±0.5 mkUNIT/ml). By the 5$^{th}$ minute after stimulation, concentration of insulin in hepatic vein was returning to the initial level, and from the 15$^{th}$ minute it was decreasing significantly, which, presumably, indicates post-stimulation depletion of insulin-producing function of newborn rabbits islet cells cultures implanted to the portal system of liver.

These results demonstrate a substantial insulin-producing ability (in response to stimulation by glucose) of beta-cells of islet cells cultures xenotransplanted into recipient's liver and its possible ability to function on the principle of "feed-back reaction".

Proof of functioning of transplanted beta-cells of pancreases of newborn rabbits was demonstrated by this original (unique) method because it is yet impossible to detect production of insulin by transplant based on secretion of C-peptide, due to lack of existence in the world of sets for immune-radiological or immune-ferment identification of C-peptide of rabbits.

Example 13

General Results of Xenotransplantation of Cultures of Pancreatic Insular Cells to Rats with Experimental Diabetes Mellitus Ability of cultures of pancreatic insular cells, received through the original method from pancreases of newborn rabbits, to survive and function in in-vivo environment, has been demonstrated by us in experiments of xenotransplantation of such cultures to animals with experimental Diabetes Mellitus.

Vistar Line male rats of body mass of 180-220 gm, regularly fed, were used as experimental animals. Experimental Diabetes Mellitus was provoked by sub-dermal application of Alloxan (dosage 200 ml for 1 kg of body weight) or by sub-dermal application of Streptozotocini (dosage 60 ml/kg). During experiments and control probes we used only rats with Alloxan or Streptozotocin-induced Diabetes, those whose level of hypoglycemia on empty stomach was 20 mmol/l and higher. Earlier conducted tests indicated that such animals did not have spontaneous reversion of experimental Diabetes Mellitus.

After transplantation of pancreatic islet cells cultures, 88 out of 104 rats with stable or severe Alloxan-induced Diabetes Mellitus (almost 85%) displayed firm remission of diabetic status up-to the end of experimental term (20 weeks). Firm decrease of blood sugar levels of almost-up-to-normal levels was registered in blood of animals-recipients. At the same time, characteristic clinical symptoms of diabetes were also vanishing (such as weight loss, polydipsia, polyuria). Anti-Diabetic effect of Xenotransplantation was clearly demonstrated both in cases of application of cultures into liver (through portal vein or directly into liver's parenchyma) and also into spleen (cultures were brought in intra-pulp.), and also through the abdominal muscles. Even after 8 weeks after Xeno-transplantation, pancreatic islet cells with preserved structure and with signs of secretory activity was detected in places of implantation in rats with remission of experimental Diabetes.

During special series of experiments the role of preliminary cultivation of pancreatic islet cells in vitro was demonstrated clearly in survival of cells in organisms of xenogeny recipient. For that purpose, we performed comparative analyses of results of xenotransplantation of cultures of pancreatic islet cells of pancreas of human fetuses and xeno-transplantation of non-cultivated fetal Island tissue to rats with experimental Diabetes Mellitus. It was detected that sugar-reducing effect is more expressed and long-lasting in cases of transplantation of pre-cultivated pancreatic islet cells in comparison with transplantation of non-cultivated tissue of Pancreas, which results only in short-lived remission of Diabetic status. So, the immune-modulating result of cultivating in vitro was experimentally proven to significantly increase the term of survivability in an organism of alien recipient.

Pancreases of 18 rats-recipients, on whom successful xenotransplantation of cultures of Pancreases of newborn rabbits had been performed, were subjected to histological exam in 8 weeks after transplantation. For that purpose a fragment of pancreas was fixated in Buena solution and was drown in paraffin. Slices (5-7 mkm thick) were colored by hematoxilin and eosin, and also by Aldehyde-fuchsine for revealing of β-cells. At the same time, pancreases of 6 control animals who had untreated alloxan-induced Diabetes as well as pancreases of 6 healthy rats (no Alloxan applied) were closely examined.

While examining pancreases of healthy intact rats, some 45 to 76% of beta-cells, as expected, were found in "Langerhans" islands. Rats with untreated Alloxan-induced Diabetes had sharply decreased amount of β-cells in Islands—in average 8.3+−1.1%.

Significantly higher amount of beta-cells in islands was discovered in rats-recipients. In animals, who had been subjected to xenotransplantation of pancreatic islet cells cultures, their own Pancreases displayed typical β-cells and its share among "island" cells was from 10 to 55% (some from 7 to 21%) (average 23.5±8.8%).

With regards to these experiments, we may assume that anti-diabetic effect of xeno-transplantation of OK cultures on developments of experimental diabetes in rats is occurring 2 general ways: a.) Functioning of transplanted β-cells, confirmed, in addition to expressed sugar-reducing effect, also by revealing groups of transplanted pancreatic islet cells in the pulp of spleen of animals-recipients; b.) Stimulating effect of transplantation of Pancreatic islet cells cultures on the Island apparatuses of pancreas of rats-recipients, which possibility is confirmed by data of histological exams revealing existence of significantly frequent of Islands with normal β-cells and bigger share of them in Islands of pancreas of rats-recipients than of rats with untreated Alloxan-induced Diabetes. Successful experimental research became grounds for performing clinical transplantation of islet cells of pancreas of newborn rabbits to Diabetes-type-1 patients.

Example 14

Clinical Transplantation of Cultures of Pancreatic Islet Cells Produced from of Pancreases of Newborn Rabbits Total of 112 patients with Type-1 Diabetes Mellitus (Insulin-dependent diabetes mellitus—IDDM) were under well-documented dynamic supervision. Of total of 112 patients there were 58 men, and 54 women. Patients' age at the moment of transplantation varied from 16 to 53—average 35 years old.

It is known that severity of manifestation of secondary diabetic complications depends significantly on duration of the insulin-dependent diabetes mellitus. Supposedly, destruction of own β-cells of the patient as a result of autoimmune process approximately happens on the 5$^{th}$ year after manifestation of the disease. Secondary diabetic complications manifest itself usually in patients with duration of disease of more than 10 years. Because of that, all insulin-dependent diabetes mellitus patients were divided in 3 groups in reference to duration of the disease: a.) 1 to 5 years—16 people; b.) 6 to 10 years—43 people, c.) more than 10 years—53 patients. All patients had been examined with the aim to determine character of development of insulin-dependent diabetes mellitus and establishing presence of diabetic complications.

Usually OK cultures received through the above-described methods out of 50-60 pancreases of 1-2 day newborn rabbits were used for transplantation for one patient. Suspension was usually delivered into transverse abdominal muscle under local anesthesia. No immune suppression was used.

Below are the results of xenotransplantation of pancreatic islet cells cultures on the course of development of insulin-dependent diabetes mellitus, on expression of its complications in patients of different duration of the disease.

Transplantation of Cultures of Pancreatic Islet Cells of Newborn Rabbits to Patients with Insulin-Dependent Diabetes Mellitus from 1 to 5 Years 5 out of 16 patients of this group had insulin-dependent diabetes mellitus with sharply labile character. 2 of them had frequent (several a week) spontaneous (without known provoking reasons) hypoglycemic conditions, which caused numerous inpatient treatment attempts, but all attempts to stabilize course of disease or to determine insulin dosage were to no avail. 3 patients had labile insulin-dependent diabetes mellitus with possibility of development hardly-eliminating ketoses; attempts to reach metabolic compensation yield only short-lived effect.

Three patients (2 of them with labile Diabetes Mellitus) revealed symptoms of sensori-motor neuropathy-paresthesia and pulling pain in calf-muscles. After intramuscular xenotransplantation of pancreatic islet cells cultures, majority of patients noticed reduction in usually elevated day-average glycemia levels during 2-4 weeks. Retention of its value within the range corresponding to good compensation of carbohydrate metabolism (average 7.8 to 9.9 mmole/kg) was noted further during at least 12 months of post-transplantation supervision. On this, in all 5 patients with labile IDDM the course of the disease acquired stable nature: predisposition to hypoglycemic conditions and ketosis disappeared. Improvement of glycogenic control after transplantation of cultures of pancreatic islet cells of newborn rabbits confirms the information on determination of glycozylated hemoglobin in recipients' blood (reduction from pre-transplantation 12.4% to 9.6%, 8.3 and 10.1% relatively to 6,9—and 12 months after transplantation. Elevation of insulin-dependent diabetes mellitus compensation and clear tendency to reduction of average daily level of glycemia allowed us by the end of the $1^{st}$ month to somewhat reduce dosage of administered insulin (average 12%), which remained to some degree reduced in 3, 6, 9 and 12 months after transplantation—relatively for 31.5%, 36.2%, 25.5%, and 18.4%. On this, 3 patients' requirements in exogenous insulin decreased between $4^{th}$ and the months after transplantation for more than 50% (from 54% to 86%), at the same time for 2 patients the doze of administered insulin by the 1-3 month of post-transplantation period was temporarily (for 2-4 week term) somewhat increased for 13% and 12%.

Because in patients with history of the insulin-dependent diabetes mellitus of less than 5 years possibility of presence of own β-cells exists, we would expect evaluation of residual secretion of C-peptide prior to transplantation (analyses were performed automatically with the help of immune-ferment method, which usual parameters of content of C-peptide in blood serum is 0.5-3.5 ng/ml). It turned up that prior to transplantation only 3 out of 6 patients (19%) had no secretion of C-peptide neither basal (on empty stomach) no stimulated (by standard breakfast). Duration of their insulin-dependent diabetes mellitus history was longer than 3 years. Average level of basal and stimulated C-peptide in patients with disease duration from 1 to 5 years (including zero exponents in 4 of them) accounted for relatively 0.12 and 0.36 ng/ml. After transplantation in 2 out of 3 "C-peptide-negative recipients" concentration was registered—first stimulated, then (by the $3^{rd}$ month)—a basal secretion of C-peptide, which indicated a restoration of insulin secretion by own β-cells of the patient. "C-peptide-positive recipients" demonstrated substantial increase of C-peptide content in blood serum, which in 5 patients even reached the normal factor. It is important to point that by the end of the $1^{st}$ year of observation there was no expressed tendency to depletion of C-peptide in recipients' blood. Such were the changes noted during the 12 months after the first transplantation to insulin-dependent diabetes mellitus patients with history of disease duration of 1 to 5 years.

Nine patients from this group with average interval of 13.3±1.8 months were subjected to repeated intramuscular transplantations of pancreatic islet cells cultures of newborn rabbits: 1 patent three times, 3 patients—twice, and 5 patients—one time. No one of these patients displayed neither local nor general signs of rejection/disengagement of a transplant, nor any allergic reactions.

Eight out of 9 patients, who had been subjected to repeated transplantation revealed therapeutic effect of no lesser value than in initial transplantation. In 3 out of 4 patients, who were subjected to xenotransplantation of pancreatic islet cells cultures thrice (i.e. +2 repeated times) increment of clinical effect was noted, such as increase in muscle mass and significant improvement of life tonus. In this, stable course of insulin-dependent diabetes mellitus preserved, and symptoms of secondary diabetic complications were absent. The only one patient in this group who sustained 4 transplantations (by the end of this experiment history of his disease was longer than 9 years) during the 5,5, years of observation demonstrated no signs of destabilization of the course of disease (prior to $1^{st}$ transplantation it was sharply labile), and still no signs of diabetic angiopathy. It seems like accrued effect of repeated transplantations is governed by increase in secretory activity of own Island Apparatus of recipients confirmed by increase of concentration of both basal and stimulated human C-peptide with each transplantation.

Transplantation of Cultures of Pancreatic Insular Cells of Newborn Rabbits to Patients with Disease History of 6 to 10 Years.

Total of 43 insulin-dependent diabetes mellitus patients with duration of disease from 6 to years were under supervision (average duration 7.8 years); 24 men and 19 women. Age of patients at the moment of first transplantation was in the range from 15 to 43 years (average 28.3). 12 patients had a sharply expressed labile character of the disease, which had not been stabilized during several attempts of inpatient treatment. 16 patients had secondary symptoms of insulin-dependent diabetes mellitus complications; 9 of them had only sensorimotor neuropathy and developing nephropathy (Mogensen stage 3), 2 patients—had autonomous neuropathy (predisposition to tachycardia), and 2 recipients—developed non-proliferating retinopathy.

In 1-2 months after xenotransplantation all 12 patients with prior labile insulin-dependent diabetes mellitus status changed to more controlled and manageable status. Usually, stabilization of indexes of carbohydrate metabolism occurred also. As such, prior to transplantation, recipients' daily average blood glucose was fluctuating between 9.6 to 14.1 mmol/l, but in 1 month after transplantation the daily glycemia was 6.6. to 11.2 (average 8.6 mmol/l). Maximal reduction of this index was noted by the 3-month term (7.8 mmol/l), but by the end of the 1 year term it still remained satisfactory—at a level of 8.8 mmol/l).

Improvement in compensation of carbohydrate metabolism was confirmed by change of amount of glucozylated hemoglobin in patients' blood from 12% prior to transplantation (average) its level in 3 months was already 10.8%, in 6 months—9.4%, in 9 months—somewhat increased (to 10.9%), but by the year's end reduced again to 9.8%.

Also, in majority of patients in this group a forced decrease of daily administered insulin doze in comparison with the pre-transplantation level: in 3 months after the transplantation it decreased in average for 15.22%, in 6 months—for 30.1%, in 9 months—27.0%, in 12 months—25.1%.

Despite significant insulin-dependent diabetes mellitus history in this patients' group (from 6 to 10 years—in average 7.8), only approximately 75% (32 patients) prior to transplantation had had no own insulin secretion (C-peptide completely absent). Because other patients in this group had basal level of C-peptide varied from 0.05 to 0.2 ng/ml, and stimulated—from 0.1 to 0.3 ng/ml, its average concentration in the group before transplantation was on empty stomach—0.07 and after stimulation—0.08 ng/ml. After transplantation, steady increase of C-peptide concentration in blood was occurring—in 3 months basal level was in average same 0.07 and stimulated level—already 0.11 ng/ml; in 6 months—more than 3-time increase—relatively up to 0.38 and 0.43 ng/ml, but by the $9^{th}$ month—decrease up to 0.09 and 0.13 ng/ml.

During post-transplantation period, there were signs of more positive course of secondary complications in this group's recipients. Symptoms of both—sensori-motor and autonomous neuropathy started to weaken already by the end of 1-1.5 month after xeno-transplantation, and almost stopped bothering patients by the $3^{rd}$ month. Also, in both patients with diabetic nephropathy a protein-urea disappeared completely by 2-4$^{th}$ month after transplantation, and it did not reoccur for almost a year after the transplantation. Patients with diabetic retinopathy did not register increase in pathological changes in fundus of the eye.

Repeated transplantations (in 7-13 months after the $1^{st}$ transplantation) were performed on 14 patients: 1 time on 5 patients, twice on 5 patients, three times on 4 patients, and 4 repeated transplantations—on 1 patient. In majority of cases repeated transplantations of pancreas insular cells, in minimum, contributed to preservation of positive changes in patients' status that had occurred after the $1^{st}$ transplantation. Specifically noted shall be the result of successive (interval 7-9 months) 5 transplantations in patient with severe sensori-motor neuropathy, which had led 48-year-old man (with Insulin-dependent diabetes mellitus history of 8 years) to severe deconditioning (incapacitation/inability to wok) due to severe pain in extremities and expressed muscular atrophy, especially in lower extremities. After $1^{st}$ transplantation pain in extremities lessened, and then after the $2^{nd}$ transplantation it completely vanished, and then muscular tonus and volume began to regenerate. As a result of performed transplantation, during the 4.5 years of observation the patient's muscular volume expanded for 23 kg, his muscular tonus normalized, as well as conductance of nerve impulse through motor nerves. Also, Diabetes acquired stable course; doze of introduced insulin decreased for 50%. It is possible, that reduction of exogenous insulin was significantly stipulated by significant revival of own B-cells of the patient, as human C-Peptide content in recipient's blood—0.1 ng/ml (empty stomach) and 0.1 ng/ml (stimulated) prior to that became relatively 0.36 and 0.55 ng/ml by the end of the 4-year period of post-transplantation observation.

Transplantation of Pancreatic Insular Cells Cultures of Newborn Rabbits to Patients with Disease History of More than 10 Years.

This group consisted of 53 persons—32 women and 21 men. Patients' age at the moment of the first transplantation varied from 21 to 53—average 33.4. Duration of disease varied from 11 to 27 years (average 14.8).

9 patients had true labile course diabetes: spontaneous hypoglycemic conditions often alternated with ketone-acidosis episodes.

There were secondary diabetic complications discovered in 38 patients: 11 had only sensori-motor neuropathy; 1 patient had sensori-motor neuropathy and diabetic cataract, 5 patients—sensori-motor neuropathy, initial nephropathy (in Mogensen) and non-proliferating diabetic retinopathy; 8 patients—arising nephropathy and non-proliferating retinopathy; 6 patients—expressed nephropathy and pre-proliferating retinopathy; 2 patients—arising nephropathy and proliferating retinopathy; 2 patients—expressed nephropathy and proliferating retinopathy; 2 patients—sensori-motor and autonomous neuropathy, expressed nephropathy and pre-proliferating retinopathy, and 1 patient—sensori-motor and autonomous neuropathy, uremic stage of diabetic nephropathy and proliferating retinopathy.

As such, diabetic neuropathy was revealed in 23 patients, including 20 with sensori-motor and 3—with autonomous. Diabetic nephropathy was revealed in 24 patients, including arising nephropathy in 15 patients, expressed—in 8 patients, and uremic stage in 1 recipient. Diabetic retinopathy was revealed in 26 patients, including non-proliferating stage—in 13 patients; pre-proliferating stage—in 8 patients, and proliferating stage—in 5 recipients.

With the purpose of diminishing of danger of development of hypoglycemic conditions, patients with expressed stages of diabetic retinopathy and nephropathy were transplanted a dose of pancreatic islet cells cultures received from no more than 40 pancreases of newborn rabbits. All recipients with initially labile IDDM course had relatively quick (during 1-3 months) stabilization of level of glycemia, and more adequate regime of insulin-therapy was chosen.

There was a substantial reduction of average level of daily glycemia in patients of this group: from 12.8 mmol/l prior to transplantation to 9.8 mmol/l in 3 months after transplantation, and 10.1 mmol/l in 9 months after transplantation. In correspondence to changes in glycemia glucozylated hemoglobin concentration also reduced in recipients' blood from 13.1 to 10.0%.

Significant increase of degree of compensation of IDDM was accompanied by decrease in requirements of recipients in exogenous insulin. By the $3^{rd}$ months after xeno-transplantation, doze of administered insulin was reduced for patients of this group in average for 12.5%, in 6 months—for 26.6%, in 9 months—for 25.0%, in 12 months—only for 9.8%, which demonstrated that requirement for exogenous insulin to pre-transplantation level. Maximum reduction was noted in Patient C. (female) (26 years old, duration of IDDM—20 years; secondary complications—sensori-motor neuropathy, expressed nephropathy, pre-proliferating retinopathy). Already in 2 weeks after intra-muscular transplantation of pancreatic islet cells cultures received out of 40 pancreases of newborn rabbits, reduction in need for administered insulin was as such—it dropped from 36 to 24 units/day, in 6 weeks—to 16 units/day, in 10 weeks to 4 units/day (i.e. 90% reduction). At the same time on the background of stable condition, the level of daily average glycemia did not exceed 9 mmol/l. HbA1c content in 4 months after transplantation reduced to 8.7% and did not exceed 9% during the period of at least 1.5 years. At the same time, substantial reduction of expressiveness of secondary diabetic complications also occurred.

4 patients, despite their long history of IDDM (from 10.2 to 13.5 years, average 11.1 years), revealed residual secretion of C-peptide (in average 0.05 ng/ml on empty stomach, non-stimulated. However, after transplantation by the $3^{rd}$ month the amount of C-peptide-positive patients doubled up—and these 8 patients (average duration of diabetes—12.6 years) concentration of C-peptide on empty stomach was in average of 0.09 ng/ml, and stimulated—0.12.ng/ml.

Effect/influence of transplantation on degree of manifestation of diabetic complications depended in majority of cases on its types and clinical stages (advancement). So, if all patients with sensor-motor neuropathy had substantial improvement of the course of this complication already after the first transplantation of pancreatic islet cells cultures, but 2 out of 3 patients with autonomous neuropathy only second transplantation made any positive effect.

12 out of 15 patients with initial stage of diabetic nephropathy had firm disappearance of micro-protein-urea and elimination of tendency to arterial hypertension. Positive post-transplantation effect was observed in patients with expressed nephropathy almost in 63% of cases—in 5 of 8 recipients. At the same time, extraction of protein with urine significantly reduced: macro-protein-urea interchanged to micro-protein-urea (less than 0.3 g/day) and a tendency to reduction and normalization of elevated blood pressure, which allowed to significantly reduce doses of hypotensive remedies or even to terminate administering it. 2 out of 3 other recipients during the period of observation (relatively 2 and 2.5 years) there were no signs of progressive diabetic nephropathy.

A the same time a patient with the final stage of diabetic nephropathy had only a short-lived positive effect: for 4-5 weeks after xenotransplantation of cultures of pancreatic islet cells his moderately elevated level of blood creatinine and urea approached the upper border of normal indexes, after which relatively slow but firm progression of chronic kidney insufficiency took place.

10 recipients with initial and expressed stages of diabetic nephropathy were subjected to repeated transplantations of pancreatic islet cells cultures, and 4 of patients with expressed nephropathy became 3-time recipients during the 3-4 year period. 9 out of 10 patients subjected to re-transplantation were noted for at least no further progression of kidney function problems.

A patient with diabetic cataract (age 22 years old, IDDM) duration—11 years) by the $5^{th}$ month after transplantation was examined by oculists who stopped noticing spots of clouding of the crystalline lens, they evaluated this change in clinical picture as "cataract resorption".

In 10 out of 13 patients (i.e. with non-proliferating retinopathy there were no progression of pathological changes noted during the whole term of observation (from 1 to 6 years), with improvement of the eye fundus picture; in 5 recipients (absence of retina detachment, decrease of amount of micro-aneurisms.) However, in 3 patients with non-proliferating retinopathy there was increase in amount of aneurisms and regional hemorrhages occurred.

Out of 8 observed patients with pre-proliferating retinopathy, in 3 cases after 2-4 years after the only xenotransplantation of pancreatic islet cells cultures, proliferating process was noted. At the same time 3 patients of the same group (63%), who prior to transplantation had had laser-coagulation procedure performed, did not need repeated laser treatment during the whole term of post-transplantation observation—from 1 to 6 years. In this, 3 patients of this group had relatively 1, 2 and 3 repeated transplantations with interval from 9 months to 1.5 years.

After xeno-transplantation of P.I.C. Cultures, 2 out of 5 patients with proliferating stage of diabetic retinopathy had relatively long (duration 1 and 1.5 years) stabilization of clinical picture of the eyeground with moderate increase of visual functions (probably, due to active resoiption of hem-orrhages), and further progression of proliferating process was noted, herewith 1 patient (female) had repeated hem-orrhage into vitreous body with substantial worsening of visual functions.

Using transplantation of cultured islet cells produced from pancreases of newborn rabbits appeared to be very effective in children's diabetic practice. Late results of xenotransplantation of cultures of islet cells in children with type-1 diabetes mellitus were researched through observation of 20 patients prior to transplantation and in 5 years after the first transplantation (Volkov, 2005 {1}). Comparative group (control without transplantation) consisted of 20 children selected on principle "occurrence-control" with an allowance for age, sex, longevity of the disease, level of compensation, requirement in insulin and development of complications.

Catamnesis analysis demonstrated that xenotransplantation of cultures of islet cells has a positive affect on insulin requirements. Thus, already by the $3^{rd}$ month after transplantation dose of administered insulin decreased in half of recipients, in comparison with the initial level, and by the end of the $1^{st}$ year—43% of patients had lesser requirement in insulin. There were no such changes in the comparison group. Dose-response effect was noted: the most decrease in insulin requirements was noted after administration of the culture containing approximately 5 mln of beta cells. At that, in post-transplantation period more persistent and expressed compensation of carbohydrate metabolism, which is confirmed by dynamics of daily average glycemia in comparison to the control group. Already in 3 months after xeno-transplantation, level of daily glycemia reduced from 10.78±0.55 mmol/l to 8.6±0.4 mmol/l against 9.15±0.72 mmol/l (initially 10.65±0.79 mmol/l). In 1-year period after transplantation these distinctions became more meaningful: in observation group daily average glycemia is 8.5±0.39 mmol/l against 10.14±0.6 mmol/l in control group. Similar tendencies remained in cases of repeated transplantations.

Therapeutic effect of transplantation of cultures of islet cells on the course of diabetic complications proved to be extremely important. Long-term clinical observations demonstrated that, in comparison with the control group, there were less frequent occurrences of diabetic nephropathy, retinopathy, and growth disorders (as manifestation of Moriak syndrome) in children with diabetes mellitus type-1 after transplantation treatment. Thus, decrease in occurrence of retinopathy from 25% to 11% (increase in this indicator from 23% to 25% in control group). Loss of albumin with urine significantly decreased—from 207.4 to 78.7 mg/day in patients with diabetic nephropathy after xenotransplantation, whereas in comparison group this indicator kept growing—from 220.67 to 273.1 mg/day.

Such complication as Moriak Syndrome is one of the features of children's and adolescent diabetology, growth disorders included in its structure. Usage of anabolic preparations for treatment of stated pathology leads to a short-lived effect, to advancement of closing of growth zones and in reduction of final body height (growth). In the course of xenogeneic transplantation of cultures of islet cells, rapidity of growth was revealed but without change of speed in closing of growth zones. As such, share of patients having height lower than 5% (authentic nanism), decreased from 18% to 14% during the $1^{st}$ year of observation. In 5-year catamnesis, not one patient with height lower than 5 percentili among children of observation group was found. In comparison group share of undersized children increased from 20% to 22% during the $1^{st}$ year of observation. In 5-year observation, share of patients with height under 5 percentili reduced to 10% due to application of intensified insulinotherapy.

Immunological research demonstrated that xenogenous transplantation of cultures of islet cells does not cause substantial and long-term activation of autoimmune process, which is very important in application of this type of therapy in patients with partially preserved insulin-producing function. Careful observation of patients from observation group (with annual inpatient examination) did not reveal contamination of zoonosal infections, not even one.

Effect of Xenotransplantation of Cultures of Islet Cells of Pancreases of Newborn Rabbits on Immunity Indicators in Patients with Type-1 Diabetes Mellitus.

Complex immunologic research in 20 patients with type-1 diabetes was performed after completion of primary intramuscular transplantation of cultures of islet cells of pancreases of newly-born rabbits, and in 12 patients with type-1 diabetes after repeated xenotransplantations of cultures of islet cells. 17 standard tests of cellular and humoral immunity were used in immunologic research, systems of phagocytes and complement, including titer of complement-fixing antibodies towards islet cells of pancreases of newly-born rabbits.

It is proven that in patients with type-1 diabetes prior to transplantation of Islet Cells cultures activation of T-cell immunity nexus was observed, as well as presence of imbalance of immunoregulatory subpopulation of T lymphocytes, and activation of nonspecific protection factors. After transplantation 8 recipients (i.e. 40%) after the primary transplantation of OK cultures showed low KFA titer of antibodies towards total antigen OK and insulin, and 10 patients (50%) showed moderate increase of B-lymphocytes count at 2-$3^{rd}$ month, with its successive reduction.

In determining subpopulations of T lymphocytes in dynamics after xenotransplantation, there was a tendency to normalization of content of T lymphocytes by the 7-$10^{th}$ day. Amount of CD4-cells continued to decline, amount of CD3-cells continues to increase. By 14-$20^{th}$ day the number of helper T-cells measured up to normal. By the 2-$3^{rd}$ month after transplantation, the on-going normalization of indexes of cellular immunity was conjugated with achieving of good compensation of the disease.

Examinations of immune status in patients subjected to repeated transplantations of cultures of islet cells of newborn rabbits did not reveal any signs of immune response to xenotransplant. Quantitative and functional indexes of immunity were comparable to such in primary xenotransplantations.

Xenotransplantation of Cultures of Islet Cells of Pancreases of Newborn Rabbits to Patients with Recently Diagnosed Insulin-Dependant Diabetes Mellitus.

Type-1 diabetes mellitus patients with history of disease of longer than 5 years usually become recipients of OK cultures; they practically lack insulin-producing activity of own islet apparatus of pancreas, and in majority of cases secondary diabetic complications are advanced in different stages.

However, hopeful results were achieved also after intramuscular transplantation of cultures of islet cells of pancreases of newborn rabbits to patients with recently diagnosed diabetes mellitus type-1.

10 young people (average age 18±02 years) with average history of diagnosed diabetes (6±0.2 month). Positive results in glycemia control were noted in all patients during the 6-8 months after xenogenous transplantation (fasting glycemia 5.2±0.2 mmol/l, after food intake—7.0±0.15 mmol/l, daily glucosuria—0.25±0.03 grams, HbA1—5.8±0.2 mmol/l). Daily dose of exogenous insulin was reduced from 0.62±0.11 to 0.28±0.2 units at 1 kilogram of body weight. 7 patients (i.e. 70% cases) during the post-transplantation period had partial and 2 recipients (i.e. 20% cases)—full remission of diabetic status (induces by transplantation "honeymoon" of diabetes mellitus type-1), which continued for 4-8 months. At that, increased in pre-transplantation period levels of glucagons and growth hormone in recipients blood normalized (glucagons concentration decreased from 112.0±2.1 to 69.7±1.2 ng/ml, p<0.05; growth hormone—from 8.9±0.04 to 5.6±0.02 ng/ml, p<0.05) with successive normalization of daily profile of growth hormone. Human C-peptide concentration in patients' serum increased from 0.3±0.01 to 1.26±0.02 ng/ml; p<5; which attests to significant decrease of secretion of own insulin in recipients under the influence of performed transplantation of xenogenous islet cells. At that, patients displayed normalization of indexes of cellular and humoral immunity, which had been pathologically altered prior to transplantation (table 40)

TABLE 40

Indexes of immune status in patients with recently diagnosed IDDM after xenotransplantation of cultures of islet cells

| | Mnths Tx | OKT3 % | OKT4 % | OKT8 % | OKB7 % | OK1a % | IgA Mg % | IgM Mg % | IgG mg % |
|---|---|---|---|---|---|---|---|---|---|
| Rec n = 10 | 0 | 80 ± 5* | 50 ± 3* | 30 ± 3 | 18 ± 2* | 14 ± 2* | 250 ± 13** | 221 ± 18** | 15008 ± 22* |
| | 1 | 80 ± 3* | 51 ± 2* | 29 ± 4 | 16 ± 3 | 12 ± 2 | 212 ± 9* | 212 ± 10* | 1472 ± 14** |

TABLE 40-continued

Indexes of immune status in patients with recently diagnosed IDDM after xenotransplantation of cultures of islet cells

| | Mnths Tx | OKT3 % | OKT4 % | OKT8 % | OKB7 % | OK1a % | IgA Mg % | IgM Mg % | IgG mg % |
|---|---|---|---|---|---|---|---|---|---|
| | 3 | 66 ± 2 | 36 ± 4 | 30 ± 4 | 11 ± 3 | 8 ± 3 | 174 ± 12 | 169 ± 10 | 937 ± 13 |
| | 8 | 76 ± 4* | 48 ± 2* | 26 ± 3 | 14 ± 3 | 12 ± 2* | 217 ± 13 | 224 ± 19 | 1461 ± 12** |
| Control | Healthy | 68 ± 4 | 38 ± 5 | 30 ± 4 | 10 ± 2 | 7 ± 2 | 162 ± 16 | 151 ± 8 | 910 ± 12 |

OKT3 - T cells;
OKT4 - T helpers;
OKT8 - T suppressors;
OKB7 - B lymphocytes;
OK1a - anti-HLA-DR;
Ig—immuno-globulins;
*$p < 0.05$;
**$p < 0.001$ - in comparison with control Following general changes are observed after xenotransplantation of cultures of islet cells to patients of diabetes mellitus type-1:

Stabilization of course of labile forms of disease, which results in successful selection of adequate insulinotherapy, and to significantly increase the degree of compensation of impaired carbohydrate metabolism;

Decrease in requirements for exogenous insulin for 20-30% in ⅔ of recipients;

Progressing of late diabetic complications suspends neuropathy, nephropathy, retinopathy); involution of initial stages in more than 80% cases.

It is rational to give explanations regarding possible mechanisms of anti-diabetic effect of transplantation of cultures of islet cells of newborn rabbits. In spite of wide adaptation into practice of educating patients with type-1 diabetes mellitus to methodology of self-control of glycemia and of technique of selection of adequate doses of administered insulin, a severe labile course of disease is noted in some patients. An onset of frequent spontaneous (i.e. occurring without visible reasons) of hypoglycemic conditions often interchange by development of ketosis; and all attempts to reach metabolic compensation in these inpatients render only short-time relief. However, in 2-3 months after xenotransplantation of cultures of islet cells, practically in all cases the course of labile diabetes mellitus acquire more controllable and manageable character. At the same time, usually happens stabilization of indexes of carbohydrate metabolism and eradication of disposition to ketosis.

Apparently, stabilization of labile forms of diabetes mellitus and realization of compensation of carbohydrate metabolism are conditioned, first of all, by secretion of insulin by transplanted beta-cells. During the post-transplantation period, administered dose of exogenous insulin (usually reduced in comparison to pre-transplantation level), sort of secures basic requirement in this hormone. In turn, insulin secreted by transplanted beta-cells goes to recipient's blood more likely in correlation with fluctuations of the level of glycemia, by doing so facilitating more stable course of disease. Because significant concentration of human C-peptide are being located in 1-2 months after xenotransplantation in part of recipients with lack of signs of functioning of own beta-cells (C-peptide-negative), we may assume that patient's partially restored islet apparatus steps in the process of regulation of carbohydrate metabolism. Owing to that, in patients with previous labile course of diabetes hypoglycemic status becomes less expressive, and more often—completely disappears because transplanted and restored beta-cells stop extracting insulin in situations where glycemia approaches level close to normal. It appears, that stabilization of level of glycemia after transplantation of cultures of islet cells is conditioned by restoration, to some extent, of feedback mechanism between level of glycemia and secretion of insulin, which feedback was absent in patients with diabetes mellitus type-1 because of cell death caused by autoimmune process in islands of pancreas.

It is also possible, that some role in stabilization of IDDM and in decreasing of requirements of recipient in exogenous insulin may be attributed to normalization of insulin receptors in peripheral tissues after Islet Cells culture transplantation.

Because there was no significant reduction of requirements in exogenous insulin in considerable proportion of recipients with positive effect of transplantation of islet cells on diabetic angiopathy, it seems like reduction of administered insulin dose cannot be considered as a main, and especially, as sole sign of effectiveness of transplantation treatment. If we put a purpose of achieving full insulin-independence as an end in itself, this approach can be fraught with risk of development of clinical situations dangerous for patient. As our experience demonstrates, a single-stage administration of significantly enlarged portions of xenogenous cultures of islet cells consisting practically only from beta-cells, can provoke development of grave hypoglycemic status; but frequent (every 1-1.5 month) repeated transplantations of "regular" portions into liver (through permanent catheter to portal vein) can, at the end, lead to hardly predictable overdose of amount of transplanted beta-cells.

No adequate insulin production by beta-cells that happens, likely, because of its inability to secrete insulin on strict principle of feedback, may lead to development of serious hypoglycemic conditions, even upon withdrawal of insulin injections. As a result, emaciation of glycogenic depots in recipients and genesis of glucose by the way of glucose-neo-genesis leads to accumulation of ketonic bodies and keto-acidosis.

Stay and regress of late diabetic complications shall be considered as practically more meaningful, of greater prognostic importance, and as more achievable in reality result of transplantation of cultures of islet cells.

Of special importance is an effect of xenotransplantation of cultures of islet cells on specific for diabetes mellitus impairment of vessels—angiopathy—as they namely are the main reason of loss of sight (diabetic retinopathy).

Effect Mechanism of Islet Cells Transplantation on Late Diabetic Complications.

It is known that formation of diabetic angiopathies is very possible even in cases of ideal compensation of carbohydrate metabolism (norm-glycemia, a-glucosuria, normal concentration of glycozylated hemoglobin) achieved with the help of intensified insulinotherapy. At the same time, after transplantation of islet cells cultures, in spite of retention of elevated concentration of glycozylated hemoglobin in blood of significant numbers of patients, in majority of cases we see slowing-down of progress and partial regress of late diabetic complications. That's why positive effect of islet cells transplantation cannot be explained, namely, by improving of indexes of carbohydrate metabolism.

In patients with insulin-dependent diabetes mellitus complicated by retinopathy the severity of changes on eye fundus is growing as secretion of insulin by patient's own pancreas decreases. Excretion of endogen insulin was judged, certainly, on concentration of C-peptide secreted into patient's blood in equimolar to insulin amounts. We suggested that progression of retinopathy was governed not only by reduction in secretion of insulin, but also by decrease in concentration of C-peptide. After allogenous or xenogenous islet cells cultures transplantation in recipient with insulin-dependency caused by death of beta-cells of own pancreas, transplanted beta-cells started to emit into patient's blood C-peptide (sure, simultaneously with insulin) which he had been deprived of during several years, when, as in the capacity of so-called substitution therapy he was getting injections of insulin preparations only. In addition, in majority of patients in post-transplantation period partial regeneration of pool of the recipient's own beta-cells takes place (Skaletskyy N. N., and others, 1994 {6}.), which, naturally, start secreting insulin and C-peptide. As a result, years-lasting deficit of C-peptide in the body is corrected, and that deficit might have been responsible for development of late specific impairment of vessels and nerves.

Assumption of physiological role of C-peptide is at odds with widely-accepted opinion that main role of C-peptide is purely structural, connecting, and presented in facilitation of folding molecules of pro-insulin in such fashion that disulphide bonds between aminoacid remains of A- and B-chains of insulin molecules formed; and that C-peptide possesses no biological potential, and as such is a ballast molecule in physiological context.

Our assumption is supported by Swedish researches (Wahren J et al., 1991 {15]). They demonstrated that C-peptide render stimulating effect on utilization of glucose by organism of insulin-dependent diabetes patient, although inhibiting influence on production of glucose by liver is not excluded. Lengthy (4 week) administering of C-peptide to type-1 Diabetes mellitus patients assured better glycemic control (judging from concentration of glucose in fasting blood and on content of glycozylated hemoglobin. In comparison with patients treated only with insulin. Very important is the data showing that administering of human C-peptide has positive influence on late complications of insulin-dependent diabetes mellitus. As such, in patients with diabetic nephropathy their renal function is improving, which improvement is demonstrated in reduction of excretion of albumin and reduction in glomerular filtration; in patients with diabetic retinopathy penetrability of hemato-retinal barrier moves upwards; patients with autonomous neuropathy has slowing down of cardiac rate on inspiration and expiration. In addition, under the influence of administering of C-peptide, blood flow in working skeletal muscles of diabetes mellitus patients improves. Mechanism of such angio- and neuro-protective effect of C-peptide is unclear. As physiological effect of C-peptide is realized through promotion of function of cell membrane, then, apparently, it pertains to activation of Na+K+–ATF (adenosine triphosphoric acid)—connected with membranes of different cells.

In conclusion, it worth pointing out that islet cells transplantation in type-1 diabetes mellitus is a very important, but auxiliary method of therapy of type-1 diabetes mellitus. Anti-diabetic treatment shall be integrated. Correct combination of reasonable diet, graded physical exercise, adequate sugar-reducing therapy is necessary for the success. Application of organ transplantation of pancreas or grafting of islets detailed from pancreas, are fully justified in providing medical help to patients with diabetic nephropathy in its terminal stage when there is a need for transplantation of an allogenous kidney. At the earlier stages of kidney impairment, and also in cases of diabetic nephropathy, retinopathy (except terminal stages), use of xenotransplantation of cultured islet cells generated from pancreases of newborn rabbits may be very effective.

Duly application of cultured islet cells transplantation in complex (integrated) treatment of type-1 diabetes mellitus may substantially affect the prognosis of critical illness. Prophylactics and deceleration of secondary diabetic complications, achieved with the help of regular repeated transplantation, can render not only medical but significant socio-economic effect by prevention or pulling off disabilities in diabetic patients and by raising their life-expectancy and longevity.

Classical method of coloring of cells on Mallori and by aldehyde-fuchsine was used for revealing beta-cells. For more specific detection of insulin-containing cells (beta-cells) we lately use immune-fluorescent method of morphologic analysis. Below is the description of basic components and phases of this method.

Immune-Histochemical Coloring of Islet Cells Cultures of Pancreas of Newborn Rabbits.

For beta-cells identification we use cultures received during incubating of pancreatic micro-fragments in plastic cultural Petri dishes (Corning-Costar). Suspension of cultivated cells and cellular clusters is washed three times from growth medium with the help of warm solution of phosphate buffer (PBS). Then, cultures are fixated with 0.5% Formalin solution during 20 minutes at room temperature. Then, cultures are perfused with PBS solution with added fetal serum (cow) till concentration reaches 1%, and incubate it during 60 minutes at room temperature for blockage of nonspecific sorption of antibodies. After 3-time cleansing with PBS solution, mouse monoclonal antibodies to insulin (Sigma) diluted by PBS solution with 5% of fetal cow serum, are laid on cultures. After that Petri dishes with studied cultures are incubated for 120 minutes at room temperature. Then, 3-time cleansing in PBS and $2^{nd}$ antibodies are laid on cultures (anti-mice antibodies marked FITC), sustaining 45-minute exposition. After that, cultures are thrice cleansed in PBS. Then, 60% solution of glycerin and PBS is laid on cultures, and put it under cover glass. Ready preparations are examined with fluorescent microscope and are photographed by digital camera.

Performed series of immune-histo-chemical analysis of islet cells cultured from pancreases f newly-born rabbits demonstrated that share of insulin-containing cells in cultures comprises from 78% to 90% (average—82.2%). Percent was calculated by counting cells in its analysis in faze contrast and then upon comparative analysis in luminescent microscope. In addition to islet cells, singular fibroblasts are found in the culture but their share, usually not exceeds 1-5%. Cells of epithelial origin are usually remaining cells in culture and make 5-17%, which fact the immune-histochemical coloring (with monoclonal antibodies against protein CytoKeratin 18) confirms; but they are not beta-cells, as these cellular structures are not revealing presence of insulin. Probably, they are just other types of islet cells whose presence in the culture shall be considered highly physiological as they (alpha-cells, delta-cells, pp-cells) are natural surroundings for beta-cells, who in normal conditions comprise, to some extent, an autonomous morpho-physiological structure—Langerhants islands.

In addition to studying the cellular composition of the culture, we determined total amount of cells in it. By the way of methodical counting in more than 20 cultures, which calculation was performed at the time of analysis under inverted microscope (Nikon, Japan) we succeeded to determine that culture received out of 20 pancreases of 1-2-day-old rabbits contains from 451600 to 568900 islet cells (average—521,500). One dose of Islet Cells Culture represents a fusion of 4 cultures of islet cells received from 80 pancreases of 1-2-day-old rabbits. Amount of islet cells containing in such a dose is, in average not less than 2,000,000, at least 80% of which are beta-cells.

Cultures, produced through the above-described method are not cellular preparation with strictly determined quantitative characteristics, such as precise percentage of beta-cells in each culture. This is not a preparation as a result of strictly regulated chemical synthesis or gene-engineering manipulations. Cellular preparation used for transplantation, represents a fusion of parallel grown cultures of islet cells, which, naturally are distinctive from each other to some degree. Analysis of cell composition, mainly rendering an idea of share of beta-cells in the culture demonstrated that it makes 80-94% while viability of these cells is from 77% to 85%. For biologic preparation this variation in figures is, in our opinion, not significant. Upon increase of amount of cultures used for 1 transplantation this variation may be reduces.

Immediately prior to a planned clinical transplantation (transportation) of islet cells culture, there is a selection of cultures with emphasis on longevity of its cultivation, results of microscopic observation, and express-analysis for sterility and viability. Gathering cultures for transplantation is conducted in conditions of laminar box securing supply of constantly circulating sterile air. Selected cultures—at 4 cultures for one transplantation dose is gathered with the help of a special cellular scraper (Cell scraper, Corning-Costar). Gathered cellular suspension is being centrifuged in special 50-milliliter plastic test-tubes (800 rotations per minute for 10 minutes). Then cellular sediment is transferred to a sterile plastic 15-mm test tube and is being suspended in a salt Hank's solution. Marked test-tube with cellular preparation is then placed into 50-mililiter test-tube and tightly closed with a lid additionally fixating it with a special film (Parafilm).

While the invention has been described in detail and with reference to specific examples thereof, it will be apparent to one skilled in the art that various changes and modifications can be made therein without departing from the spirit and scope thereof.

BIBLIOGRAPHY/LITERATURE

1 Volkov I. E., Skaletskyy N. N., Schenev S.V./Preliminary results of xenogeneic transplantation of cultures of islet cells of pancreas of rabbit to children with insulin-dependent diabetes mellitus.//Bulletin of Experimental Biology & Medicine.—1998.—No3. Volume 126. P.105-108

2. Gavrilova N. A., Skeltskyy N. N./Effect of xenotransplantation of pancreatic islet cells on pathogenic mechanisms of development and course of diabetic retinopathy.//Reporter of Transplantology & Artificial Organs.—2004.—No1—P. 30-36.

3. Skaletskaya G. N., Kirsanova L. A., Skaletskyy N. N., and others./Change of course of experimental diabetic nephropathy under influence of xenotransplantation of islet cells cultures. Materials of the III All-Russian Conference on Transplantology & Artificial Organs.//Reporter on Transplantology & Artificial Organs.—2005.—No3.—P. 47.

4. Skaletskyy N. N., Kirsanova L. A., Blyumkin V. N./Producing cultures of islet cells of pancreases and its transplantation.//Issues of Transplantology & Artificial Organs.—M., 1994.—P. 73-80.

7. Skaletskyy N, N., Shumakov V.I./Transplantation of islet cells in treatment of diabetes mellitus//Transplantation of fetalissues and cells./Bulletin of Experimental Biology & Medicine.—1998.—T.126.—Suppl. 1.—P. 109-114.

8. Shumakov V. I., Blyumkin V. N., Skaletskyy N. N., and others. Transplantation of pancreatic islet cells.—M. Canon, 1995.—P.384.

9. Shumakov V. I., Skaletskyy N. N./Regulation of carbohydrate metabolism and correction of impairment of carbohydrate metabolism at diabetes Mellitus.//Essay on physiological problems of transplantology and use of artificial organs/Under edition of Academician V.I. Shumakov.—Tula: Repronix Ltd., 1998.—P.93-118.

10. Shumakov V. I., Skaletskyy N. N. Transplantation of islet and other endocrine cells.//Transplantology (under edition of Academician V.I. Shumakov).—M: Medicine, 1995.—P. 317-331.

12. Gill R. G., The Immunology of Pancreatic Islet Transplantation.—in book "Type 1 Diabetes", Oxford University Press, 1996.—P.118-133

13. Shapiro A. M. J., Lakey J. R. T., Paty B. W., et al./Strategic opportunities in clinical islet transplantation//Transplantation.—2005.—Vol. 79.—P.1304-1307.

14. Shapiro A. M. J., Lakey J. R. T., Ryan E. A., et al./Islet transplantation in seven patients with type 1 diabetes mellitus using a glucocorticoid-free regimen//New England J. of Medicine.—2000. V.343.—P.230-238.

15. Wahren J., Johansson B.-L., Wallberg-Henriksson H./Does C-peptide have a physiological role?//Diabetologia.—1994.—37, suppl. 2.—P.99-107.

16. Shumakov V. I., Skaletskyy N. N., Evseev Yu. N. et al./Intraportal xenotransplantation of islet cell cultures in diabetic patients//Biomaterial Living System Interactions.—1993. Vol. 1.—N4.—P.179-184.

17. George S. Eizenbarth, Kevin J. Lafferty. Type I Diabetes—Molecular, Cellular & Clinical Immunology.—Oxford University press.

What is claimed is:

1. A method of obtaining beta-islet cells from pancreases of rabbits, the method comprising:
   harvesting pancreases of newborn rabbits and placing the pancreases in a salt solution comprising an antibiotic at a temperature of 4-10° C.;
   removing vessels and excretory ducts from the harvested pancreases;
   obtaining minced pancreatic micro fragments from said pancreases;

incubating said minced pancreatic micro fragments in a serum free medium at a first incubation temperature 36.6° C. to 37° C. for 6 to 10 days at 0% to 5% CO2; for a first incubation period and periodically replacing the serum free medium and removing spontaneously destroyed unwanted cells comprising exocrine cells and blood cells and elements of connective tissue until at least 80% of remaining cells are beta-islet cells; and incubating said minced pancreatic micro fragments in said serum free medium at a second incubation temperature 22° C. to 29° C. for 4 to 5 days for a second incubation period until 78-90% of remaining cells are beta-islet cells, wherein said serum free medium is optionally periodically replaced, and thereby obtaining islet cell clusters wherein 78-90% are beta-islet cells.

2. The method of claim 1, wherein the second incubation temperature is 24° C.

3. A composition exhibiting reduced immunogenicity when transplanted in a recipient isolated by a method comprising:

harvesting pancreases of newborn rabbits and placing the pancreases in a salt solution comprising an antibiotic at a temperature of 4-10° C.;

removing vessels and excretory ducts from the harvested pancreases;

obtaining minced pancreatic micro fragments from said pancreases; and incubating said minced pancreatic micro fragments in a serum free medium at a first incubation temperature 36.6° C. to 37° C. for 6 to 10 days at 0% to 5% $CO_2$ for a first incubation period and periodically replacing the serum free medium with fresh serum free medium and removing spontaneously destroyed unwanted cells comprising exocrine cells and blood cells and elements of connective tissue until at least 80% of remaining cells are beta-islet cells; and incubating said minced pancreatic micro fragments in said serum free medium at a second incubation temperature 22° C. to 29° C. for 4 to 5 days for a second incubation period until 78-90% of remaining cells are beta-islet cells, wherein said serum free medium is optionally periodically replaced with fresh serum free medium, and thereby obtaining islet cell clusters wherein 78-90% of the cells are beta-islet cells.

4. A composition comprising beta-islet cells of claim 3 and a pharmaceutically acceptable carrier.

5. A method to promote natural insulin production method comprising: preparing the composition of claim 3 comprising the beta-islet cells isolated and cultured from rabbit pancreases; and administering the composition of claim 3 to a subject in need of insulin and therefore promoting natural insulin production.

6. A composition isolated by a method comprising:

harvesting said pancreases of newborn rabbits and placing pancreases in a salt solution comprising an antibiotic at a temperature of 4-10° C.;

removing vessels and excretory ducts from the harvested pancreases;

obtaining minced pancreatic micro fragments from said pancreases; and incubating said minced pancreatic micro fragments in a serum free medium at a first incubation temperature 36.6° C. to 37° C. for 6 to 10 days at 0% to 5% CO2 for a first incubation period and periodically replacing the serum free medium with fresh serum free medium and removing spontaneously destroyed unwanted cells comprising exocrine cells and blood cells and elements of connective tissue until at least 80% of remaining cells are beta-islet cells; and incubating said minced pancreatic micro fragments in said serum free medium at a second incubation temperature 22° C. to 29° C. for 4 to 5 days for a second incubation period until 78-90% of remaining cells are beta-islet cells, wherein said serum free medium is optionally periodically replaced with fresh serum free medium, and thereby obtaining islet cell clusters wherein 78-90% are beta-islet cells.

* * * * *